US011845960B2

(12) United States Patent
Ng et al.

(10) Patent No.: US 11,845,960 B2
(45) Date of Patent: Dec. 19, 2023

(54) TRANSCRIPTION FACTORS CONTROLLING DIFFERENTIATION OF STEM CELLS

(71) Applicant: President and Fellows of Harvard College, Cambridge, MA (US)

(72) Inventors: Hon Man Alex Ng, Cambridge, MA (US); George M. Church, Cambridge, MA (US); Volker Busskamp, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 744 days.

(21) Appl. No.: 16/332,350

(22) PCT Filed: Sep. 12, 2017

(86) PCT No.: PCT/US2017/051122
§ 371 (c)(1),
(2) Date: Mar. 11, 2019

(87) PCT Pub. No.: WO2018/049382
PCT Pub. Date: Mar. 15, 2018

(65) Prior Publication Data
US 2019/0233795 A1 Aug. 1, 2019

Related U.S. Application Data

(60) Provisional application No. 62/517,307, filed on Jun. 9, 2017, provisional application No. 62/492,552, filed on May 1, 2017, provisional application No. 62/411,728, filed on Oct. 24, 2016, provisional application No. 62/393,324, filed on Sep. 12, 2016.

(51) Int. Cl.
| | |
|---|---|
| *C12N 5/071* | (2010.01) |
| *C12N 5/074* | (2010.01) |
| *C12N 5/073* | (2010.01) |
| *C12N 5/0797* | (2010.01) |
| *C12N 5/077* | (2010.01) |
| *C12N 5/0775* | (2010.01) |

(52) U.S. Cl.
CPC ........... *C12N 5/069* (2013.01); *C12N 5/0605* (2013.01); *C12N 5/0623* (2013.01); *C12N 5/0626* (2013.01); *C12N 5/0658* (2013.01); *C12N 5/0662* (2013.01); *C12N 5/0686* (2013.01); *C12N 5/0696* (2013.01); *C12N 2501/60* (2013.01); *C12N 2503/02* (2013.01); *C12N 2506/45* (2013.01); *C12N 2510/00* (2013.01)

(58) Field of Classification Search
CPC .............. C12N 5/0696; C12N 2503/02; C12N 2506/45
See application file for complete search history.

(56) References Cited

U.S. PATENT DOCUMENTS

| | | |
|---|---|---|
| 7,812,124 B2 | 10/2010 | Palm |
| 9,057,053 B2 | 6/2015 | Wernig et al. |
| 9,273,119 B2 | 3/2016 | Maizels et al. |
| 9,487,757 B2 | 11/2016 | Tesar et al. |
| 9,732,128 B2 | 8/2017 | West et al. |
| 2003/0092009 A1 | 5/2003 | Palm |
| 2004/0219575 A1 | 11/2004 | Neuman et al. |
| 2007/0161023 A1 | 7/2007 | Palm |
| 2009/0176724 A1 | 7/2009 | Shen et al. |
| 2010/0093092 A1 | 4/2010 | Bamdad et al. |
| 2011/0154518 A1 | 6/2011 | Kim et al. |
| 2012/0070419 A1 | 3/2012 | Christiansen-Weber |
| 2012/0107284 A1 | 5/2012 | Kozlova |
| 2012/0129262 A1 | 5/2012 | West et al. |
| 2012/0157474 A1 | 6/2012 | Dreyfuss et al. |
| 2012/0207744 A1 | 8/2012 | Mendlein et al. |
| 2013/0022583 A1 | 1/2013 | Wernig et al. |
| 2013/0029423 A1 | 1/2013 | Yamanaka et al. |

(Continued)

FOREIGN PATENT DOCUMENTS

| | | |
|---|---|---|
| CN | 102796696 A | 11/2012 |
| CN | 109072200 A | 12/2018 |

(Continued)

OTHER PUBLICATIONS

Rufaihah (Am J Transl Res 2013;5(1):21-35).*
Patsch (Nature Cell Biology, Aug. 2015, 17:994-1003 and 9 supplementary pages).*
Ikuno (PLOS One, 2017, 12(4):e0176238, pp. 1-18).*
Cao (Cell Death and Disease (2020) 11:859).*
Kim (Tissue Engineering and Regenerative Medicine, vol. 8, No. 2, pp. 253-261, 2011).*
Abed (haematologica 2015; 100:e431, 4 pages).*
Burdo et al., The Maize TFome—development of a transcription factor open reading frame collection for functional genomics. Plant J. Oct. 2014;80(2):356-66. doi: 10.1111/tpj.12623. Epub Aug. 26, 2014.
Busskamp et al., Rapid neurogenesis through transcriptional activation in human stem cells. Mol Syst Biol. Nov. 17, 2014;10:760(1-21). doi: 10.15252/msb.20145508.

(Continued)

*Primary Examiner* — Valarie E Bertoglio
(74) *Attorney, Agent, or Firm* — Wolf, Greenfield & Sacks, P.C.

(57) ABSTRACT

Forced expression of a handful of transcription factors (TFs) can induce conversions between cell identities; however, the extent to which TFs can alter cell identity has not been systematically assessed. Here, we assembled a human TFome, a comprehensive expression library of 1,578 human TF clones with full coverage of the major TF families. By systematically screening the human TFome, we identified 77 individual TFs that induce loss of human-induced-pluripotent-stem-cell (hiPSC) identity, suggesting a pervasive ability for TFs to alter cell identity. Using large-scale computational cell type classification trained on thousands of tissue expression profiles, we identified cell types generated by these TFs with high efficiency and speed, without additional selections or mechanical perturbations. TF expression in adult human tissues only correlated with some of the cell lineage generated, suggesting more complexity than observation studies can explain.

18 Claims, 23 Drawing Sheets

(56) References Cited

U.S. PATENT DOCUMENTS

| | | |
|---|---|---|
| 2013/0160152 A1 | 6/2013 | Ostertag et al. |
| 2013/0309769 A1 | 11/2013 | Benvenisty et al. |
| 2013/0330825 A1 | 12/2013 | Couture et al. |
| 2014/0170752 A1 | 6/2014 | Pulst et al. |
| 2014/0234971 A1 | 8/2014 | Slukvin et al. |
| 2015/0044187 A1 | 2/2015 | Visel et al. |
| 2015/0284681 A1 | 10/2015 | Wernig et al. |
| 2016/0010056 A1 | 1/2016 | Nakaki et al. |
| 2016/0038544 A1 | 2/2016 | Keller et al. |
| 2016/0201053 A1 | 7/2016 | Maizels et al. |
| 2016/0237402 A1 | 8/2016 | Tilly et al. |
| 2017/0087192 A1 | 3/2017 | Tilly et al. |
| 2018/0127714 A1 | 5/2018 | Ko |
| 2018/0289748 A9 | 10/2018 | Tilly et al. |
| 2019/0017032 A1 | 1/2019 | Firas et al. |
| 2019/0099452 A1 | 4/2019 | Jiang et al. |
| 2020/0063105 A1 | 2/2020 | Ng et al. |
| 2021/0054448 A1 | 2/2021 | Ng et al. |
| 2021/0171902 A1 | 6/2021 | Khoshakhlagh et al. |
| 2022/0204926 A1 | 6/2022 | Ng et al. |

FOREIGN PATENT DOCUMENTS

| | | |
|---|---|---|
| EP | 3118306 A1 | 1/2017 |
| JP | 2021-040578 A | 3/2021 |
| WO | WO 2004/060302 A2 | 7/2004 |
| WO | WO 2006/005043 A2 | 1/2006 |
| WO | WO 2008/153568 A1 | 12/2008 |
| WO | WO 2009/029315 A2 | 3/2009 |
| WO | WO 2009/029315 A9 | 5/2009 |
| WO | WO 2009/137674 A2 | 11/2009 |
| WO | WO 2009/137844 A2 | 11/2009 |
| WO | WO 2011/091048 A1 | 7/2011 |
| WO | WO 2012/054896 A1 | 4/2012 |
| WO | WO 2013/124309 A1 | 8/2013 |
| WO | WO 2013/170146 A1 | 11/2013 |
| WO | WO 2015/049677 A1 | 4/2015 |
| WO | WO 2015/084908 A1 | 6/2015 |
| WO | WO 2016/012570 A1 | 1/2016 |
| WO | WO 2016/103269 A1 | 6/2016 |
| WO | WO 2016/120493 A1 | 8/2016 |
| WO | WO 2016/163958 A1 | 10/2016 |
| WO | WO 2017/015075 A1 | 1/2017 |
| WO | WO 2018/049382 A1 | 3/2018 |
| WO | WO 2018/204262 A1 | 11/2018 |
| WO | WO 2019/108894 A1 | 6/2019 |
| WO | WO 2020/243392 A1 | 12/2020 |
| WO | WO 2020/243643 A1 | 12/2020 |

OTHER PUBLICATIONS

Chanda et al., Generation of induced neuronal cells by the single reprogramming factor ASCL1. Stem Cell Reports. Aug. 12, 2014;3(2):282-96. doi: 10.1016/j.stemcr.2014.05.020. Epub Jul. 4, 2014.
Chavez et al., Comparative analysis of Cas9 activators across multiple species. Nat Methods. Jul. 2016;13(7):563-567. doi: 10.1038/nmeth.3871. Epub May 23, 2016. Author Manuscript, 16 pages.
Chavez et al., Highly efficient Cas9-mediated transcriptional programming. Nat Methods. Apr. 2015;12(4):326-8. doi: 10.1038/nmeth.3312. Epub Mar. 2, 2015. Author Manuscript, 11 pages.
Choi et al., A comparison of genetically matched cell lines reveals the equivalence of human iPSCs and ESCs. Nat Biotechnol. Nov. 2015;33(11):1173-81. doi: 10.1038/nbt.3388. Epub Oct. 26, 2015. Author Manuscript, 22 pages.
Darr et al., Overexpression of NANOG in human ES cells enables feeder-free growth while inducing primitive ectoderm features. Development. Mar. 2006;133(6):1193-201.
Goparaju et al., Rapid differentiation of human pluripotent stem cells into functional neurons by mRNAs encoding transcription factors. Sci Rep. Feb. 13, 2017;7:42367(1-12). doi: 10.1038/srep42367.
Gradwohl et al., neurogenin3 is required for the development of the four endocrine cell lineages of the pancreas. Proc Natl Acad Sci U S A. Feb. 15, 2000;97(4):1607-11.
Haenebalcke et al., The ROSA26-iPSC mouse: a conditional, inducible, and exchangeable resource for studying cellular (De)differentiation. Cell Rep. Feb. 21, 2013;3(2):335-41. doi: 10.1016/j.celrep.2013.01.016. Epub Feb. 7, 2013.
Mulvaney et al., Atoh1, an essential transcription factor in neurogenesis and intestinal and inner ear development: function, regulation, and context dependency. J Assoc Res Otolaryngol. Jun. 2012;13(3):281-93. doi: 10.1007/s10162-012-0317-4. Epub Feb. 28, 2012.
Nishiyama et al., Uncovering early response of gene regulatory networks in ESCs by systematic induction of transcription factors. Cell Stem Cell. Oct. 2, 2009;5(4):420-33. doi: 10.1016/j.stem.2009.07.012. Author Manuscript, 23 pages.
Pagliuca et al., Generation of functional human pancreatic β cells in vitro. Cell. Oct. 9, 2014;159(2):428-39. doi: 10.1016/j.cell.2014.09.040. Author Manuscript, 29 pages.
Rukstalis et al., Neurogenin3: a master regulator of pancreatic islet differentiation and regeneration. Islets. Nov.-Dec. 2009;1(3):177-84. doi: 10.4161/isl.1.3.9877.
Sagal et al., Proneural transcription factor Atoh1 drives highly efficient differentiation of human pluripotent stem cells into dopaminergic neurons. Stem Cells Transl Med. Aug. 2014;3(8):888-98. doi: 10.5966/sctm.2013-0213. Epub Jun. 5, 2014.
Sripal, Combined expression of microRNAs and transcription factors for promoting hair cell differentiation. 2013 Master's Thesis. Department of Biomedical Sciences. Creighton University, 89 pages. Submitted Jul. 29, 2013.
Williams et al., SnapShot: directed differentiation of pluripotent stem cells. Cell. May 25, 2012;149(5):1174-1174.e1. doi: 10.1016/j.cell.2012.05.015. 2 pages.
Yamamizu et al., Identification of transcription factors for lineage-specific ESC differentiation. Stem Cell Reports. Dec. 2013;1(6):545-59. doi: 10.1016/j.stemcr.2013.10.006. eCollection 2013.
Zhang et al., Rapid single-step induction of functional neurons from human pluripotent stem cells. Neuron. Jun. 5, 2013;78(5):785-98. doi: 10.1016/j.neuron.2013.05.029. Author Manuscript, 24 pages.
Extended European Search Report dated Jul. 2, 2020, for Application No. EP 17849759.0.
Supplementary Partial European Search Report dated Apr. 23, 2020 for Application No. EP 17849759.0.
[No Author Listed], GenBank Submission; NIH/NCBI, Accession No. EF587698. Jul. 16, 2007. 2 pages.
[No Author Listed], GenBank Submission; NIH/NCBI, Accession No. NM_203289. Dec. 28, 2019. 4 pages.
[No Author Listed], GenBank Submission; NIH/NCBI, Accession No. EF687698. Dec. 8, 2016. 1 page.
[No Author Listed], GenBank Submission; NIH/NCBI, Accession No. NM_001173531. Dec. 28, 2019. 4 pages.
[No Author Listed], GenBank Submission; NIH/NCBI, Accession No. NM_001285986. Dec. 28, 2019. 4 pages.
[No Author Listed], GenBank Submission; NIH/NCBI, Accession No. NM_001285987. Dec. 28, 2019. 4 pages.
[No Author Listed], GenBank Submission; NIH/NCBI, Accession No. NM_002176. Dec. 31, 2019. 3 pages.
[No Author Listed], GenBank Submission; NIH/NCBI, Accession No. NM_002701. Dec. 31, 2019. 5 pages.
[No Author Listed], GenBank Submission; NIH/NCBI, Accession No. NM_005806. Sep. 27, 2019. 3 Pages.
[No Author Listed], GenBank Submission; NIH/NCBI, Accession No. NM_006168. Aug. 2, 2019. 3 pages.
[No Author Listed], GenBank Submission; NIH/NCBI, Accession No. NM_152568. Oct. 23, 2019. 3 pages.
[No Author Listed], GenBank Submission; NIH/NCBI, Accession No. NM_177400. Oct. 1, 2019. 3 pages.
[No Author Listed], GenBank Submission; NIH/NCBI, Accession No. Z46629. Oct. 7, 2008. 3 pages.
[No Author Listed], ORFeome Collaboration. The ORFeome Collaboration: a genome-scale human ORF-clone resource. Nat Methods. Mar. 2016;13(3):191-2. doi: 10.1038/nmeth.3776.

(56) References Cited

OTHER PUBLICATIONS

Adamson et al., A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.

Carstens, Identification and nucleotide sequence of the regions of Autographa californica nuclear polyhedrosis virus genome carrying insertion elements derived from Spodoptera frugiperda. Virology. Nov. 1987;161(1):8-17. doi: 10.1016/0042-6822(87)90165-6.

Chen et al., Inducing goat pluripotent stem cells with four transcription factor mRNAs that activate endogenous promoters. BMC Biotechnol. 2017;17(1):11(1-10). Published Feb. 13, 2017. doi:10.1186/s12896-017-0336-7.

Dixit et al., Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.

Douvaras et al., Generation and isolation of oligodendrocyte progenitor cells from human pluripotent stem cells. Nat Protoc. Aug. 2015;10(8):1143-54. doi: 10.1038/nprot.2015.075. Epub Jul. 2, 2015.

Ehrlich et al., Rapid and efficient generation of oligodendrocytes from human induced pluripotent stem cells using transcription factors. Proc Natl Acad Sci U S A. Mar. 14, 2017;114(11):E2243-E2252. doi: 10.1073/pnas.1614412114. Epub Feb. 28, 2017.

Fraser et al., Acquisition of Host Cell DNA Sequences by Baculoviruses: Relationship Between Host DNA Insertions and FP Mutants of Autographa californica and Galleria mellonella Nuclear Polyhedrosis Viruses. J Virol. Aug. 1983;47(2):287-300. doi: 10.1128/JVI.47.2.287-300.1983.

Garcia-Leon et al., SOX10 Single Transcription Factor-Based Fast and Efficient Generation of Oligodendrocytes from Human Pluripotent Stem Cells. Stem Cell Reports. Feb. 13, 2018;10(2):655-672. doi: 10.1016/j.stemcr.2017.12.014. Epub Jan. 11, 2018.

Gohl et al., Large-scale mapping of transposable element insertion sites using digital encoding of sample identity. Genetics. Mar. 2014;196(3):615-23. doi: 10.1534/genetics.113.159483. Epub Dec. 27, 2013.

Goldman et al., How to make an oligodendrocyte. Development. Dec. 1, 2015;142(23):3983-95. doi: 10.1242/dev.126409.

Gorbacheva et al., Improved transposon-based library preparation for the Ion Torrent platform. Biotechniques. Apr. 1, 2015;58(4):200-2. doi: 10.2144/000114277.

Hou et al., Sleeping Beauty transposon system for genetic etiological research and gene therapy of cancers. Cancer Biol Ther. 2015;16(1):8-16. doi: 10.4161/15384047.2014.986944.

Hsieh et al., PKCalpha expression regulated by Elk-1 and MZF-1 in human HCC cells. Biochem Biophys Res Commun. 2006;339(1):217-225. doi:10.1016/j.bbrc.2005.11.015.

Hui et al., Isolation and functional characterization of the human gene encoding the myeloid zinc finger protein MZF-1. Biochemistry. 1995;34(50):16493-16502. doi:10.1021/bi00050a033.

Ivics et al., Molecular reconstruction of Sleeping Beauty, a Tc1-like transposon from fish, and its transposition in human cells. Cell. Nov. 14, 1997;91(4):501-10. doi: 10.1016/s0092-8674(00)80436-5.

Jaitin et al., Dissecting Immune Circuits by Linking CRISPR-Pooled Screens with Single-Cell RNA-Seq. Cell. Dec. 15, 2016;167(7):1883-1896.e15. doi: 10.1016/j.cell.2016.11.039.

Kim et al., Oct4-induced oligodendrocyte progenitor cells enhance functional recovery in spinal cord injury model. Embo J. Oct. 23, 2015;34(23):2971-83.

Klein et al., Droplet barcoding for single-cell transcriptomics applied to embryonic stem cells. Cell. May 21, 2015;161(5):1187-1201 and Supplemental Info. doi: 10.1016/j.cell.2015.04.044.

Li et al., Neural Stem Cells Engineered to Express Three Therapeutic Factors Mediate Recovery from Chronic Stage CNS Autoimmunity. Mol Ther. Aug. 2016;24(8):1456-69. doi: 10.1038/mt.2016.104. Epub May 16, 2016.

Macosko et al., Highly Parallel Genome-wide Expression Profiling of Individual Cells Using Nanoliter Droplets. Cell. May 21, 2015;161(5):1202-1214. doi: 10.1016/j.cell.2015.05.002.

Makar et al., Stem cell based delivery of IFN-beta reduces relapses in experimental autoimmune encephalomyelitis. J Neuroimmunol. May 30, 2008;196(1-2):67-81. doi: 10.1016/j.jneuroim.2008.02.014. Epub May 8, 2008.

Morris et al., The myeloid zinc finger gene, MZF-1, regulates the CD34 promoter in vitro. Blood. 1995;86(10):3640-3647.

Najm et al., Transcription factor-mediated reprogramming of fibroblasts to expandable, myelinogenic oligodendrocyte progenitor cells. Nat Biotechnol. May 2013;31(5):426-33. doi: 10.1038/nbt.2561. Epub Apr. 14, 2013.

Neman et al., A method for deriving homogenous population of oligodendrocytes from mouse embryonic stem cells. Dev Neurobiol. Jun. 2012;72(6):777-88. doi: 10.1002/dneu.22008.

Ng, Differentiation of Human Cells and Tissues Using a Comprehensive Human Transcription Factor Library. Doctoral dissertation, Harvard University, Graduate School of Arts & Sciences. 2018. Retrieved from https://dash.harvard.edu/handle/1/41129209. 105 pages.

Pashai et al., Genome-wide profiling of pluripotent cells reveals a unique molecular signature of human embryonic germ cells. PLoS One. 2012;7(6):e39088(1-19). doi:10.1371/journal.pone.0039088.

Perrotti et al., Overexpression of the zinc finger protein MZF1 inhibits hematopoietic development from embryonic stem cells: correlation with negative regulation of CD34 and c-myb promoter activity. Mol Cell Biol. 1995;15(11):6075-6087. doi:10.1128/mcb.15.11.6075.

Selvaraj et al., Switching cell fate: the remarkable rise of induced pluripotent stem cells and lineage reprogramming technologies. Trends Biotechnol. Apr. 2010;28(4):214-23. doi: 10.1016/j.tibtech.2010.01.002. Epub Feb. 9, 2010.

Simicevic et al., Absolute quantification of transcription factors during cellular differentiation using multiplexed targeted proteomics. Nat Methods. Jun. 2013;10(6):570-6. doi: 10.1038/nmeth.2441. Epub Apr. 14, 2013.

Singari et al., Singari S, Javeed N, Tardi NJ, Marada S, Carlson JC, Kirk S, Thorn JM, Edwards KA. Inducible protein traps with dominant phenotypes for functional analysis of the *Drosophila* genome. Genetics. Jan. 2014;196(1):91-105. doi: 10.1534/genetics.113.157529. Epub Oct. 30, 2013.

Stolt et al., The Sox9 transcription factor determines glial fate choice in the developing spinal cord. Genes Dev. Jul. 1, 2003;17(13):1677-89.

Suchorska et al., Comparison of Four Protocols to Generate Chondrocyte-Like Cells from Human Induced Pluripotent Stem Cells (hiPSCs). Stem Cell Rev Rep. Apr. 2017;13(2):299-308. doi: 10.1007/s12015-016-9708-y.

Takahashi et al., Induction of pluripotent stem cells from mouse embryonic and adult fibroblast cultures by defined factors. Cell. Aug. 25, 2006;126(4):663-76. Epub Aug. 10, 2006.

Trounson, Pluripotent stem cells progressing to the clinic. Nat Rev Mol Cell Biol. Mar. 2016;17(3):194-200. doi: 10.1038/nrm.2016.10.

Van Der Maaten et al., Visualizing Data using t-SNE. J Mach Learn Res. 2008;9(86):2579-2605.

Vaquerizas et al., A census of human transcription factors: function, expression and evolution. Nat Rev Genet. Apr. 2009;10(4):252-63. doi: 10.1038/nrg2538.

Walczak et al., Directed differentiation of human iPSC into insulin producing cells is improved by induced expression of PDX1 and NKX6.1 factors in IPC progenitors. J Transl Med. Dec. 20, 2016;14(1):341. doi: 10.1186/s12967-016-1097-0.

Wang et al., Human iPSC-derived oligodendrocyte progenitor cells can myelinate and rescue a mouse model of congenital hypomyelination. Cell Stem Cell. Feb. 7, 2013;12(2):252-64. doi: 10.1016/j.stem.2012.12.002.

Yamakawa et al., Screening of Human cDNA Library Reveals Two differentiation-Related Genes, HHEX and HLX, as Promoters of Early Phase Reprogramming toward Pluripotency. Stem Cells. Nov. 2016;34(11):2661-2669. doi: 10.1002/stem.2436. Epub Jul. 8, 2016.

Yamanaka, Induced pluripotent stem cells: past, present, and future. Cell Stem Cell. Jun. 14, 2012;10(6):678-684. doi: 10.1016/j.stem.2012.05.005.

(56) References Cited

OTHER PUBLICATIONS

Yang et al., Generation of oligodendroglial cells by direct lineage conversion. Nat Biotechnol. May 2013;31(5):434-9. doi: 10.1038/nbt.2564. Epub Apr. 14, 2013.

[No Author Listed], GenBank Submission; NIH/NCBI, Accession No. NM_000572. Sep. 9, 2016. 3 pages.

Sarkar et al., The sox family of transcription factors: versatile regulators of stem and progenitor cell fate. Cell Stem Cell. Jan. 3, 2013;12(1):15-30.

Klum et al., Sequentially acting SOX proteins orchestrate astrocyte- and oligodendrocyte-specific gene expression. EMBO Rep. Nov. 2018;19(11):e46635. Epub Aug. 30, 2018.

Ng et al., A comprehensive library of human transcription factors for cell fate engineering. Nat Biotechnol. Apr. 2021;39(4):510-519. Epub Nov. 30, 2020. Author Manuscript, 37 pages.

Pozniak et al., Sox10 directs neural stem cells toward the oligodendrocyte lineage by decreasing Suppressor of Fused expression. Proc Natl Acad Sci U S A. Dec. 14, 2010;107(50):21795-800. Epub Nov. 22, 2010.

Ryu et al., Gene therapy of multiple sclerosis using interferon B-secreting human bone marrow mesenchymal stem cells. Biomed Res Int. 2013;2013:696738. Epub Apr. 22, 2013.

* cited by examiner

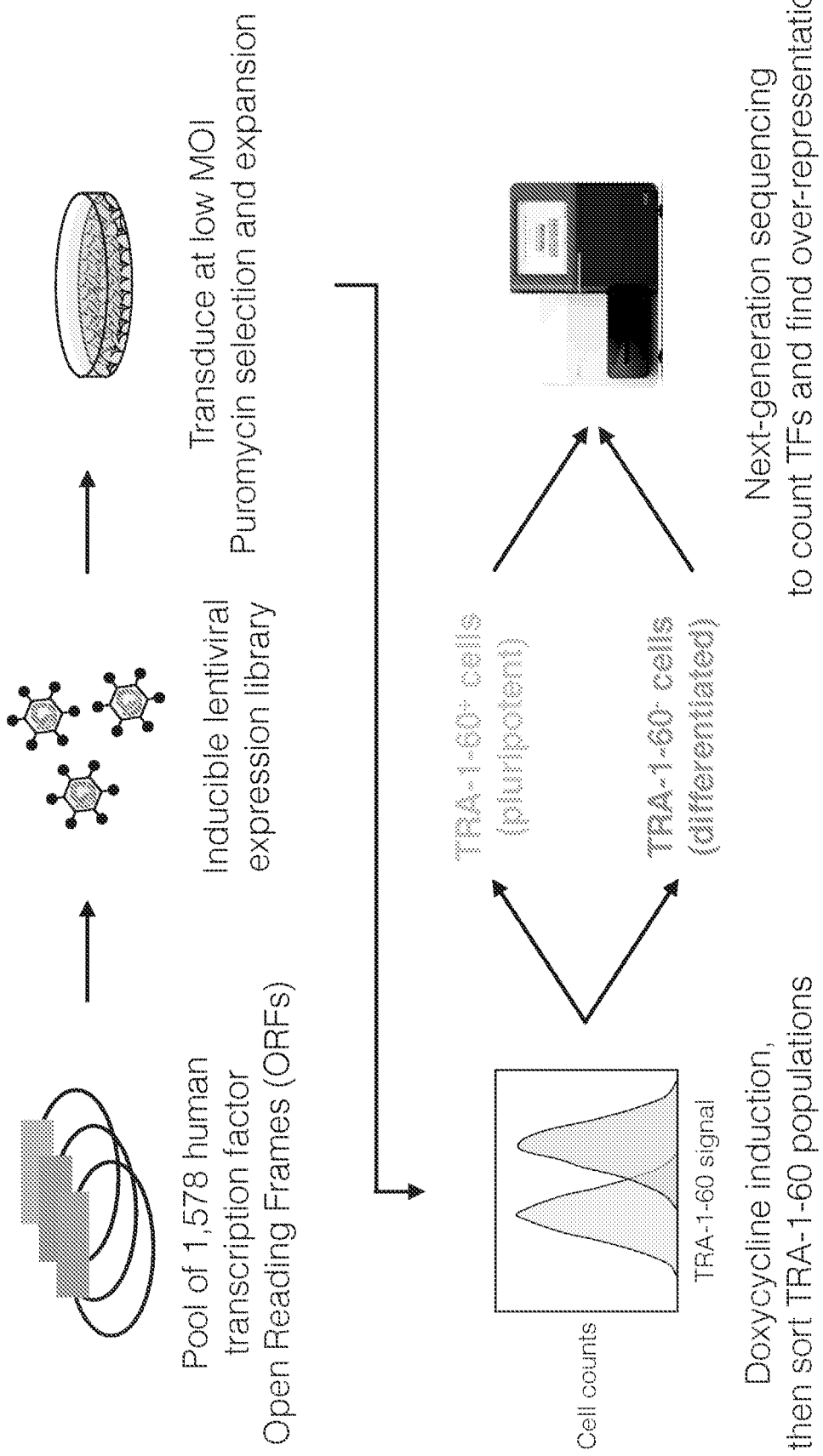

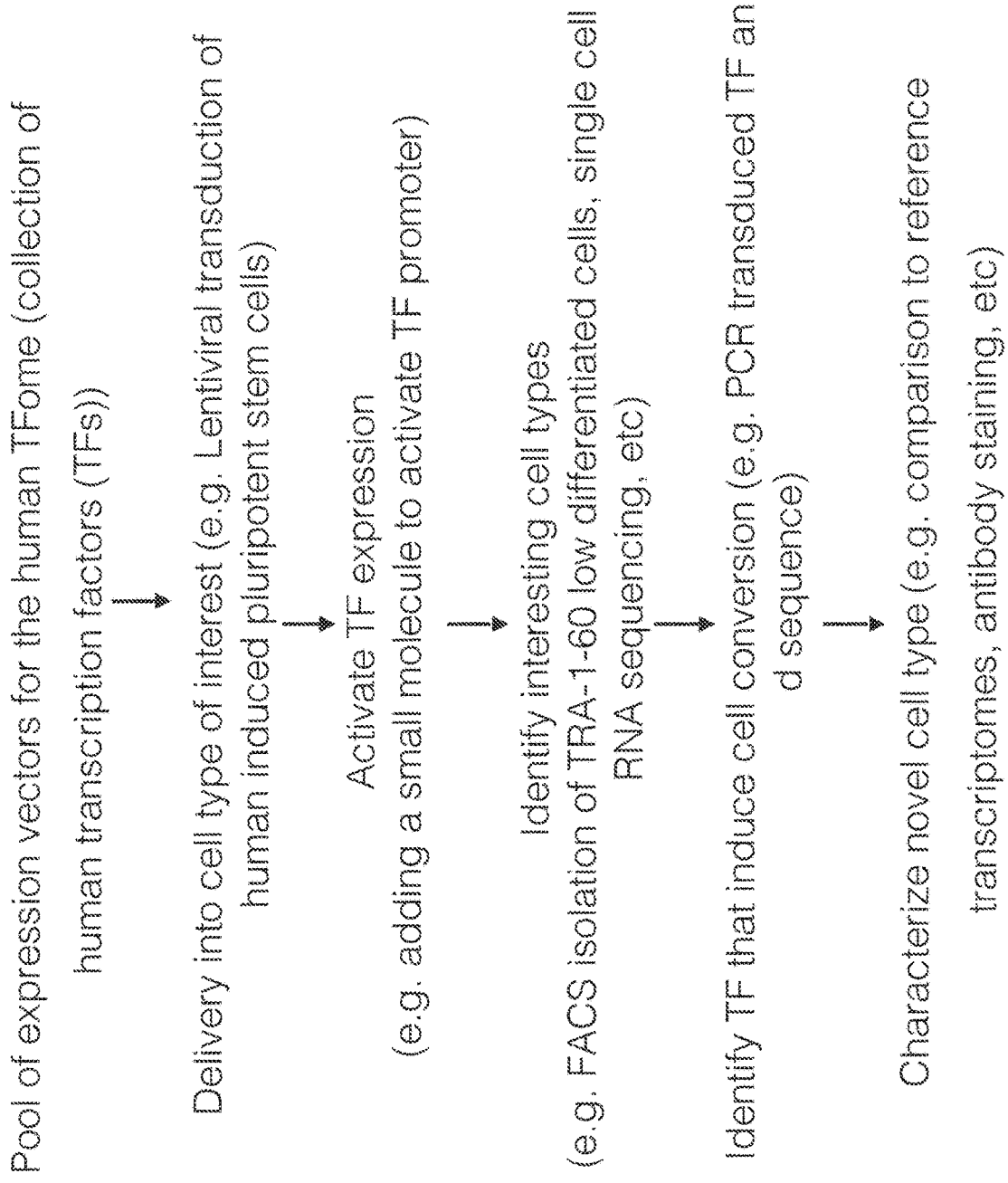
Figure 2. General strategy for high-throughput screening for cell type conversion

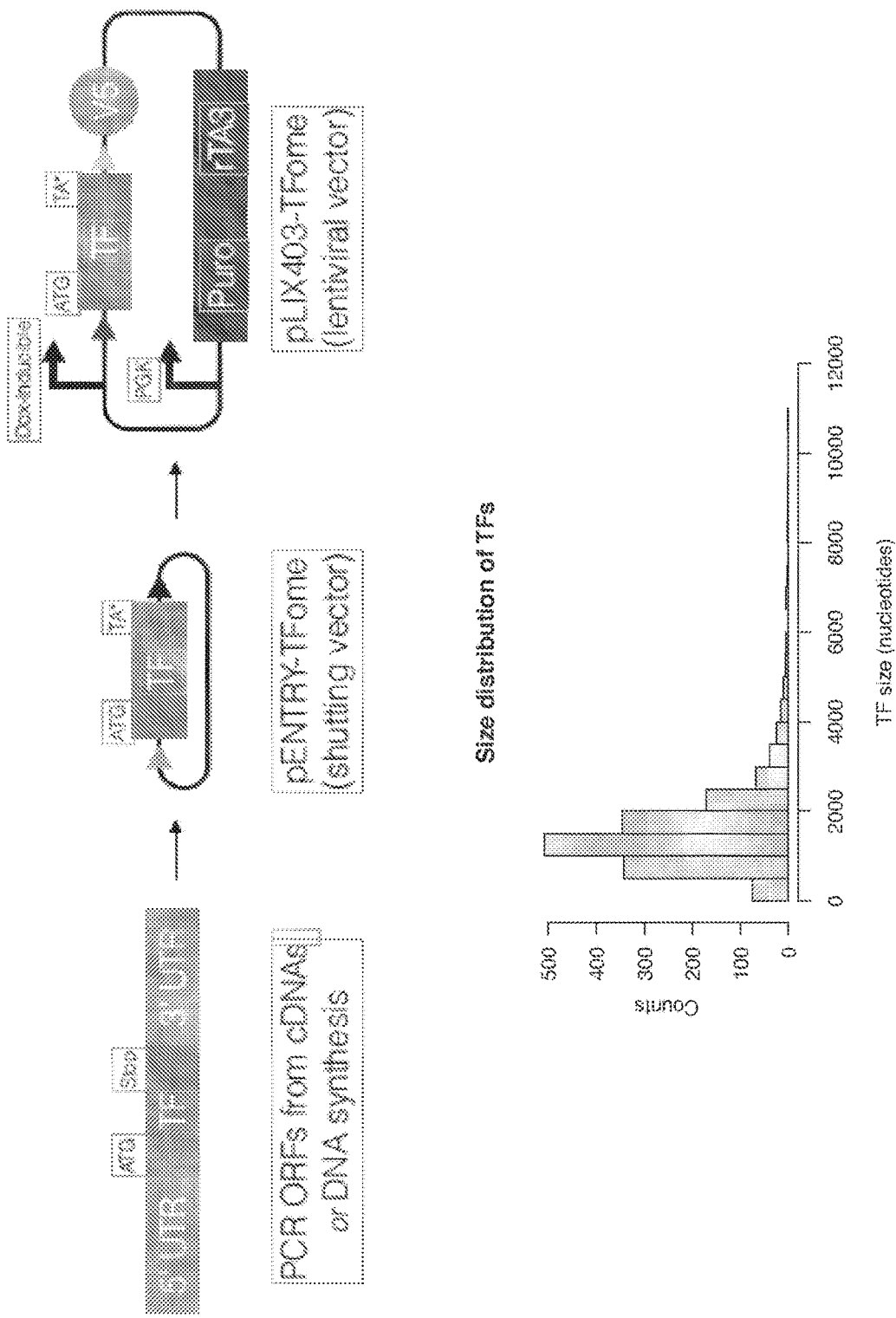

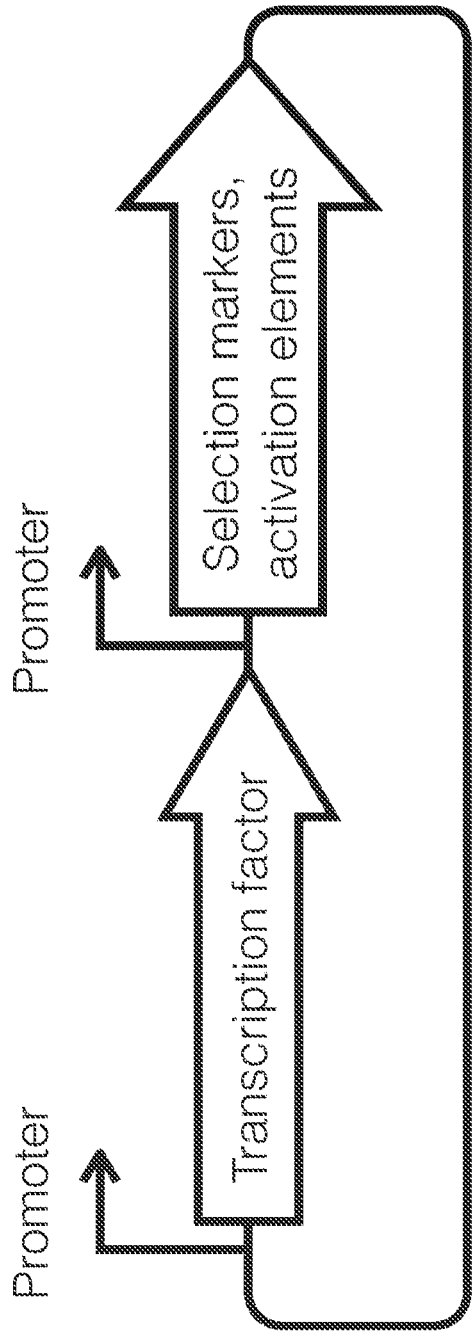

Figure 4. Expression vectors for delivery of human TFome

Example promoters:
Constitutive expression (e.g. EF1alpha promoter)
Inducible expression (e.g. small molecule, heat-shock, light) Cell type-dependent expression (e.g. neuronal promoter)

Example delivery vectors:
Transient expression (e.g. plasmid with no mammalian integration ability)
Viral vectors (e.g. lentiviral, retroviral, AAV)
Transposon-based (e.g. PiggyBac)

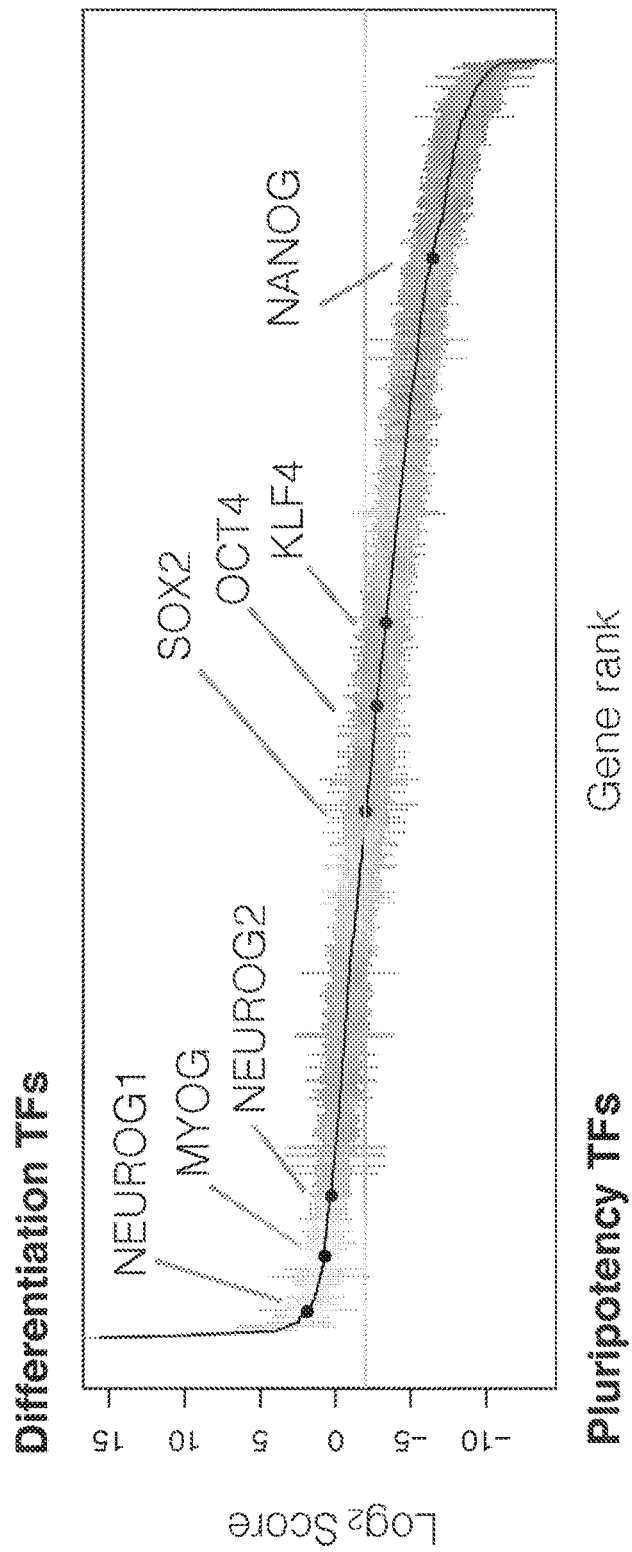
Figure 5. Hits from high-throughput screening for stem cell differentiation [loss of stem cell identity (TRA-1-60) in human induced pluripotent stem cells]

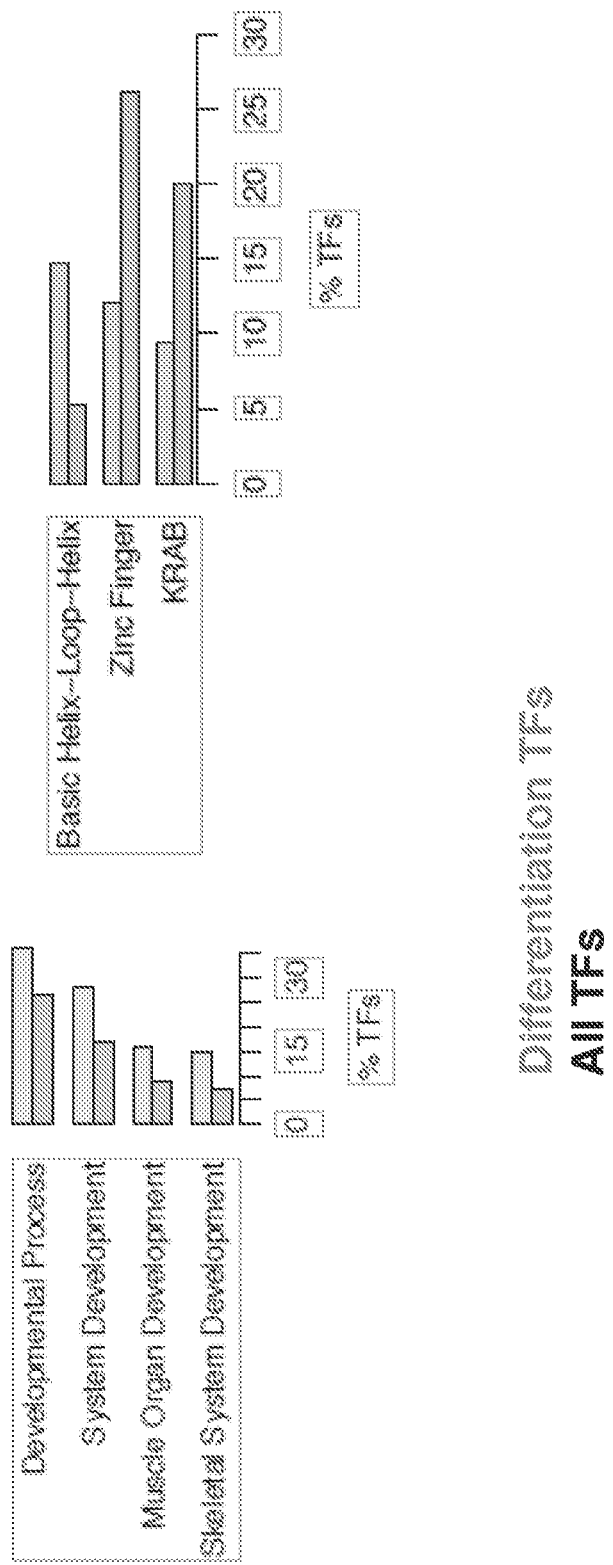
Figure 6. Hits are enriched for developmental genes and protein domains

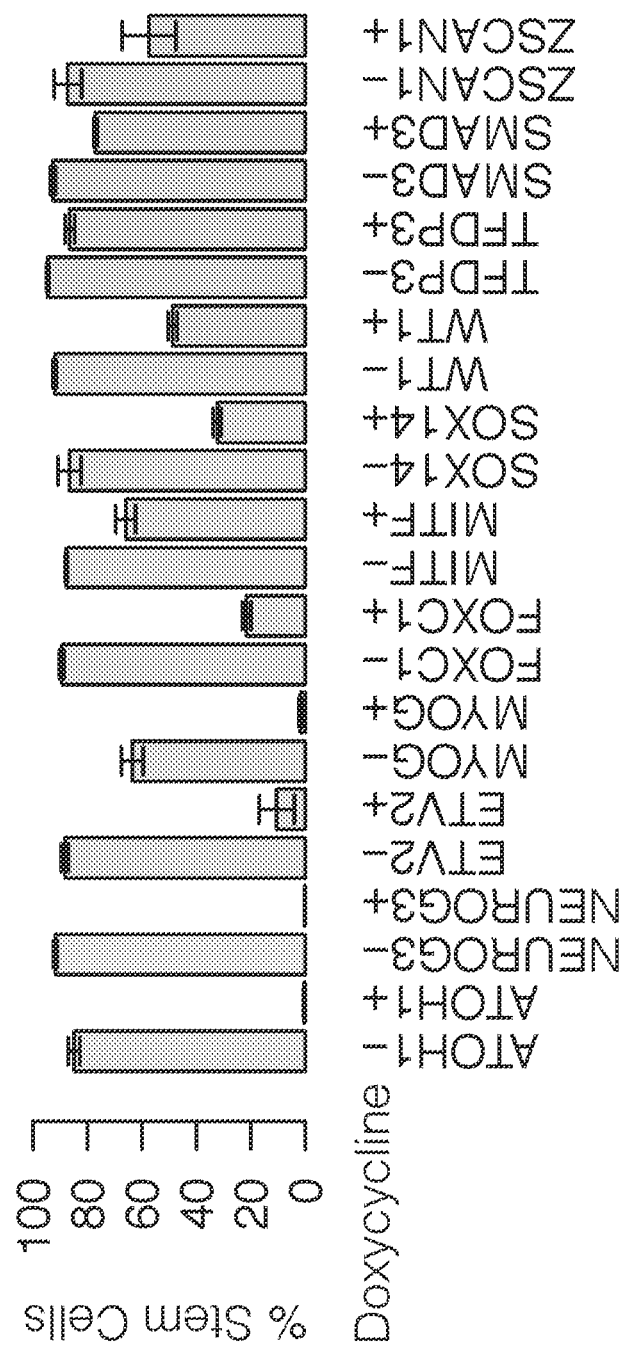
Figure 7. Selected transcription factors that induce stem cell differentiation

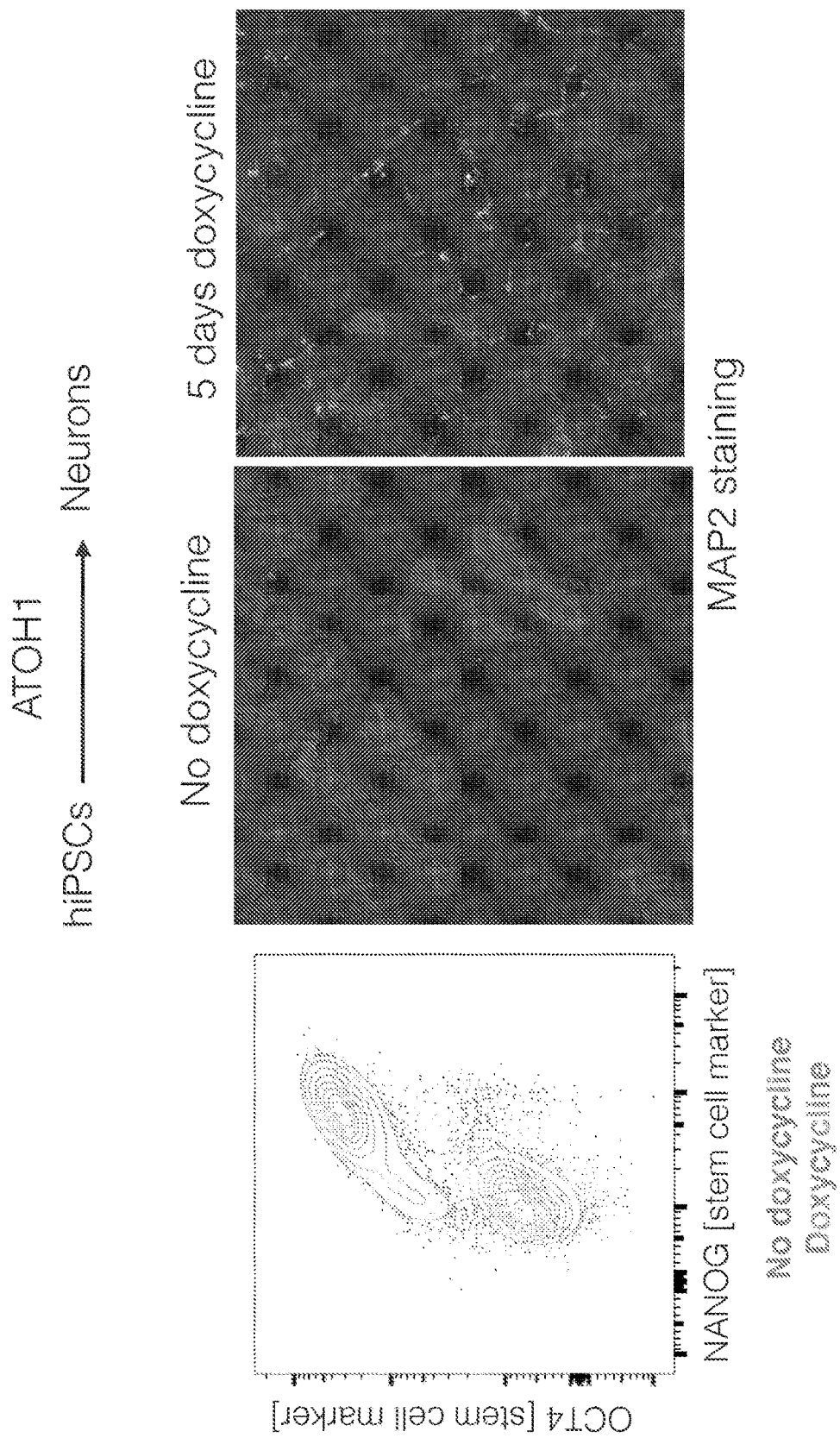
Figure 8. ATOH1 induces neuronal differentiation from hiPSCs in stem cell media without embryoid body formation, additional growth factors or mechanical manipulations

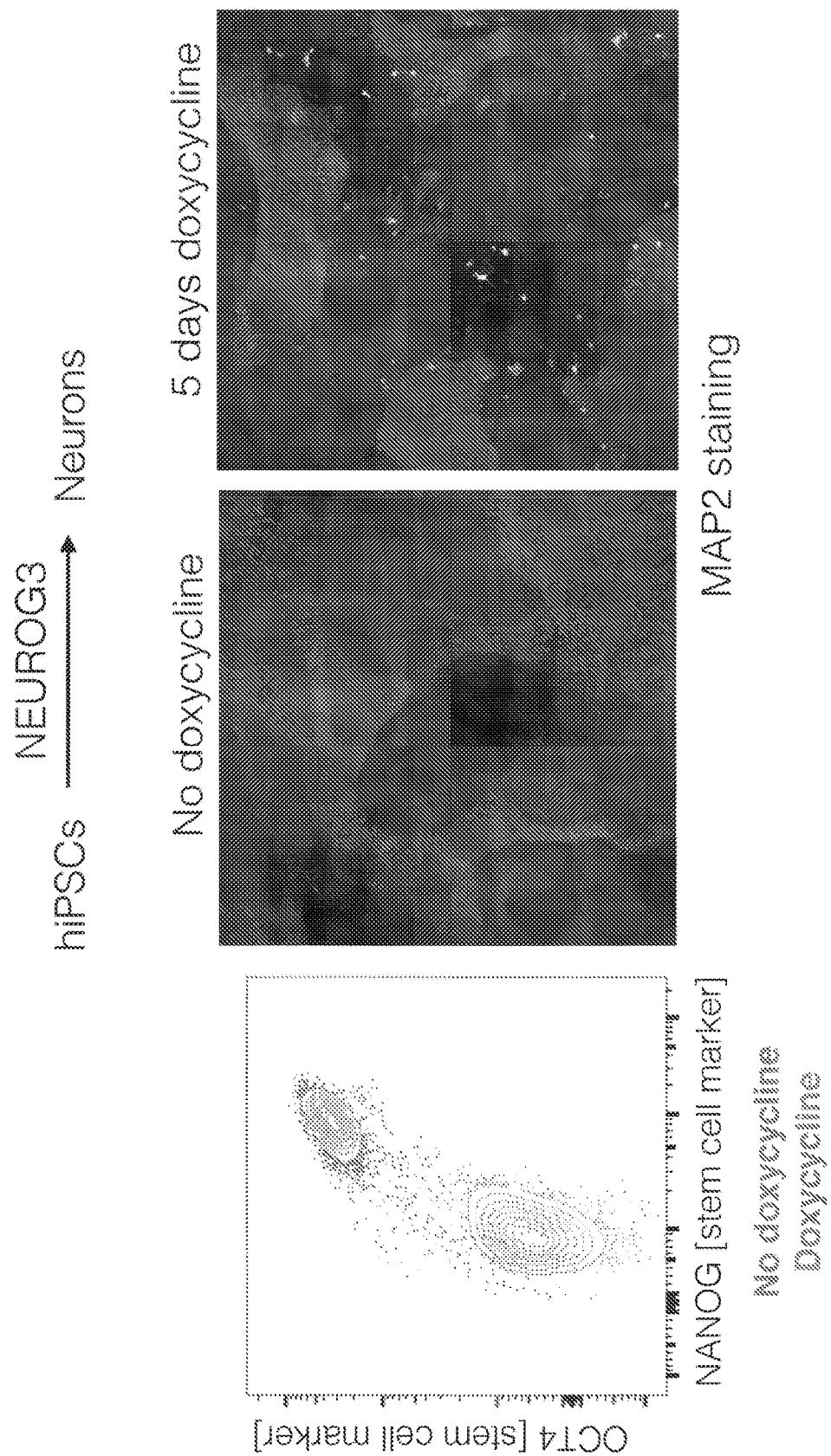
Figure 9. NEUROG3 induces neuronal differentiation from hiPSCs in stem cell media without embryoid body formation, additional growth factors or mechanical manipulations

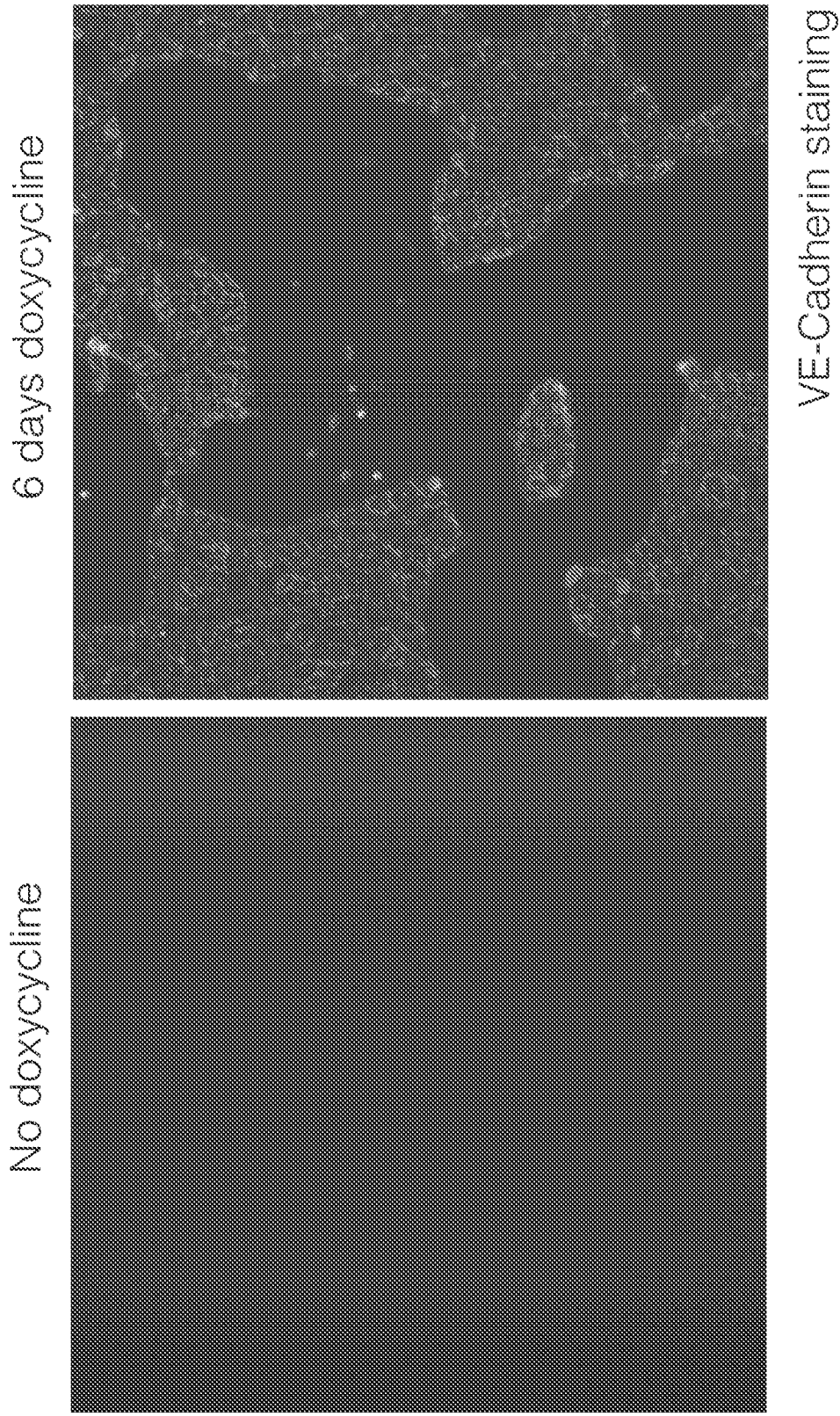

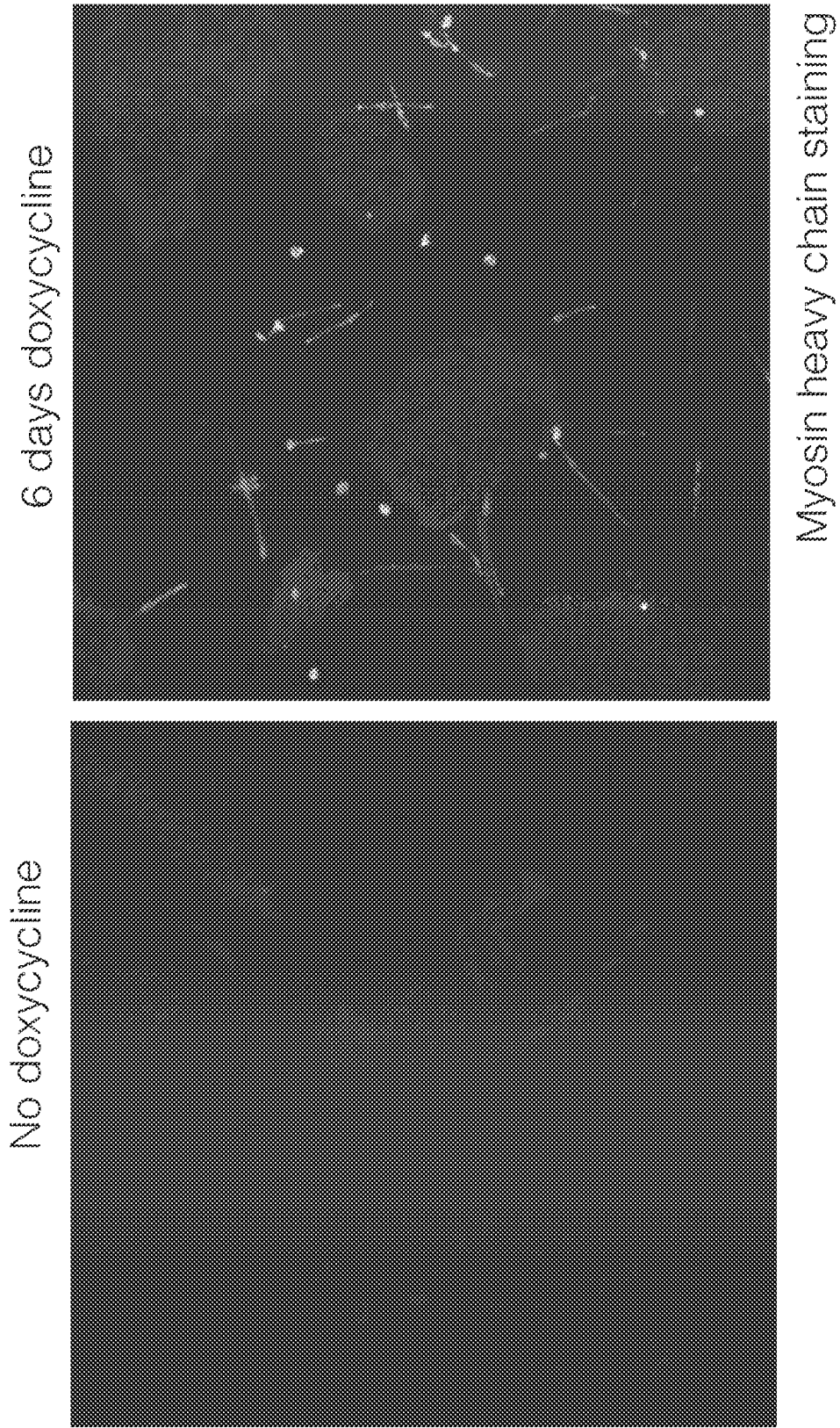
Figure 11. MYOG induces muscle differentiation from hiPSCs in stem cell media without embryoid body formation, additional growth factors or mechanical manipulations

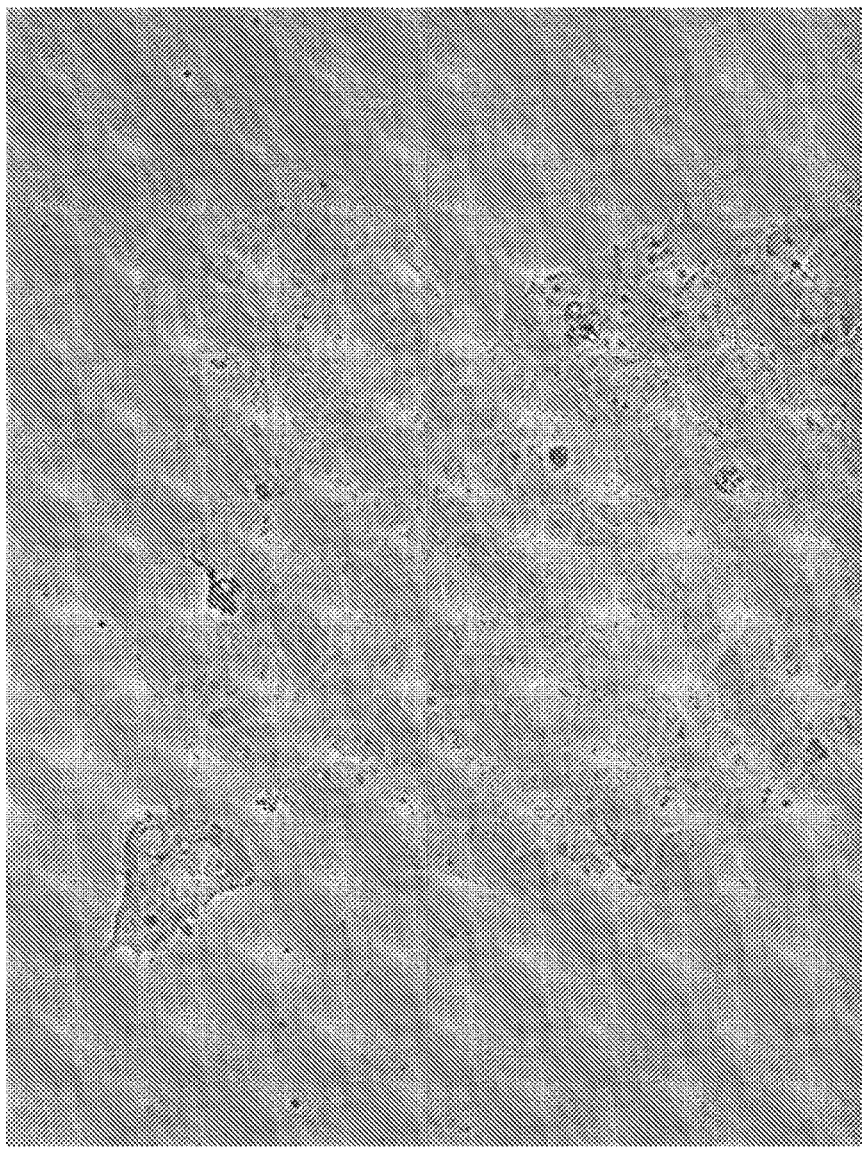
Figure 12. FOXC1 induces differentiation of hiPSCs in stem cell media without embryoid body formation, additional growth factors or mechanical manipulations
4 days doxycycline

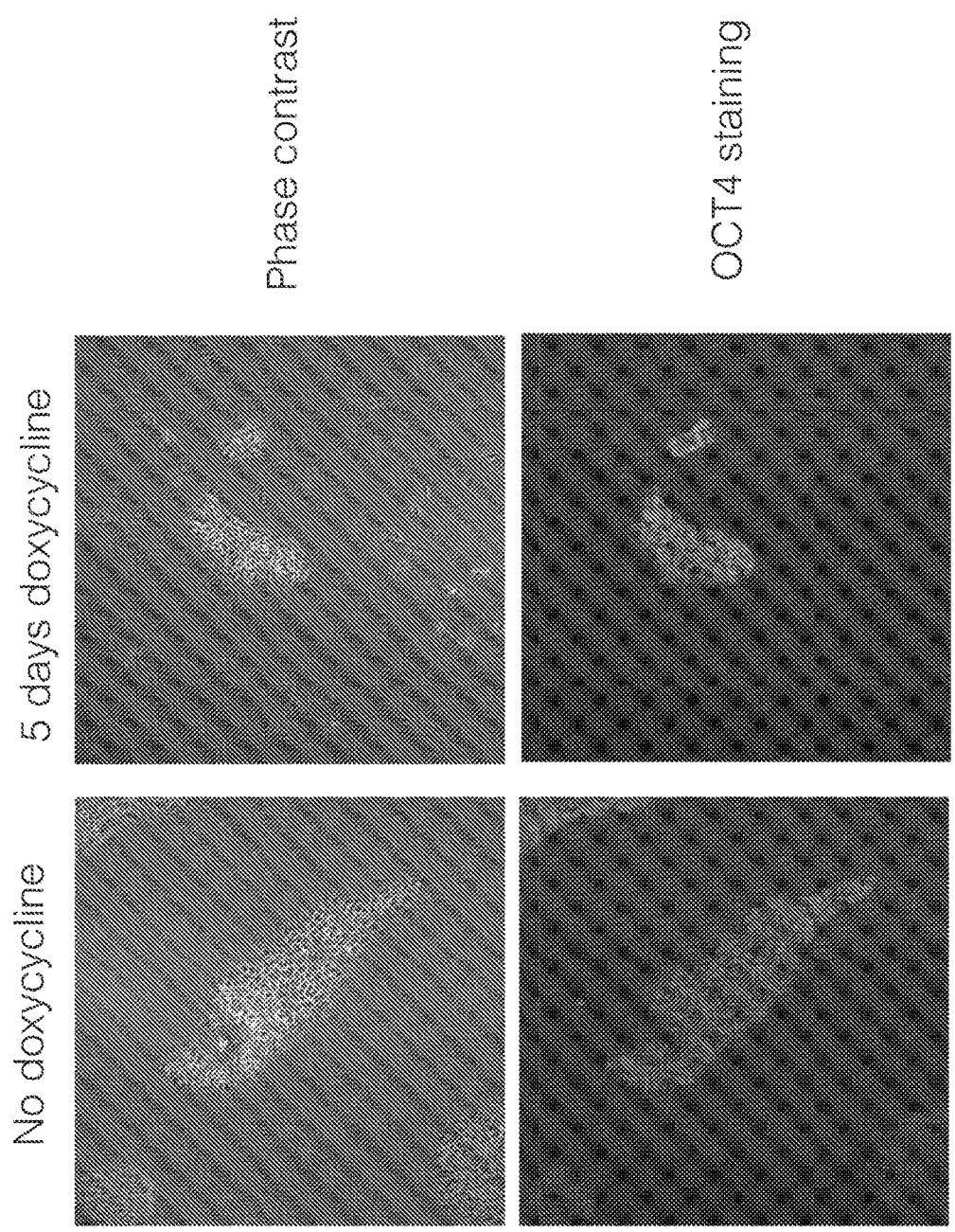
Figure 13. MITF induces differentiation of hiPSCs in stem cell media without embryoid body formation, additional growth factors or mechanical manipulations

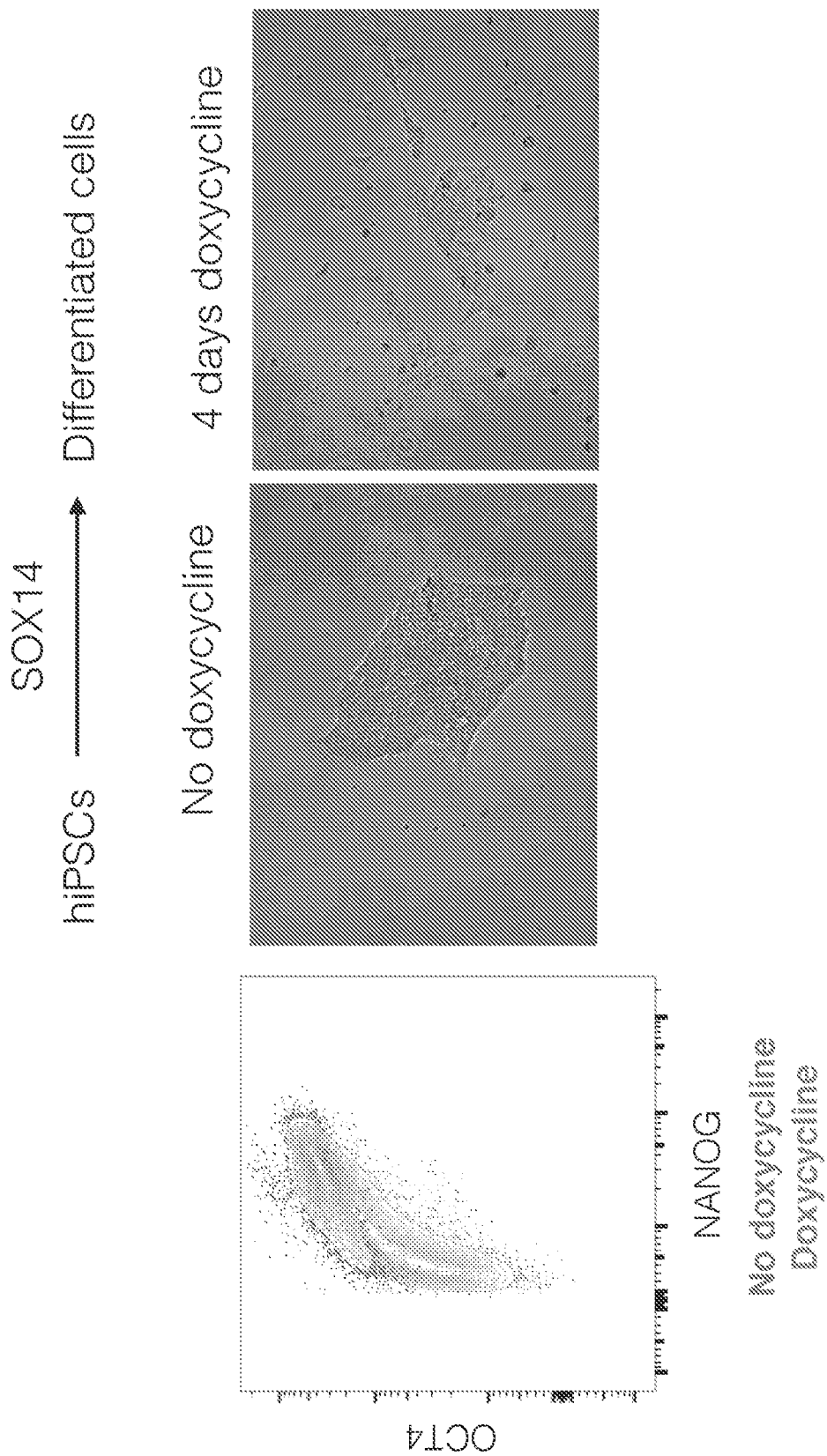
Figure 14. SOX14 induces hiPSC differentiation in stem cell media without embryoid body formation, additional growth factors or mechanical manipulations

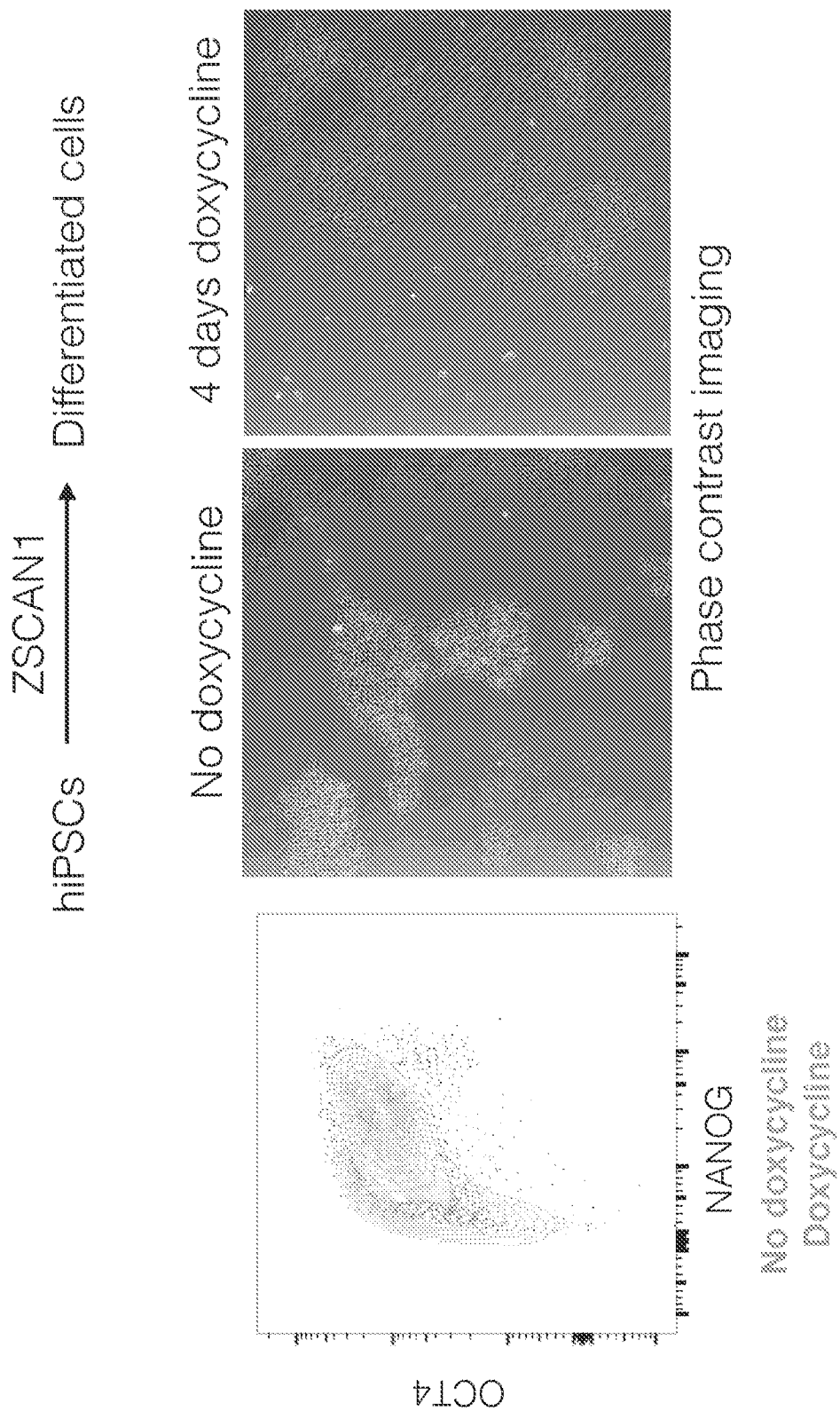
Figure 15. ZSCAN1 induces hiPSC differentiation in stem cell media without embryoid body formation, additional growth factors or mechanical manipulations

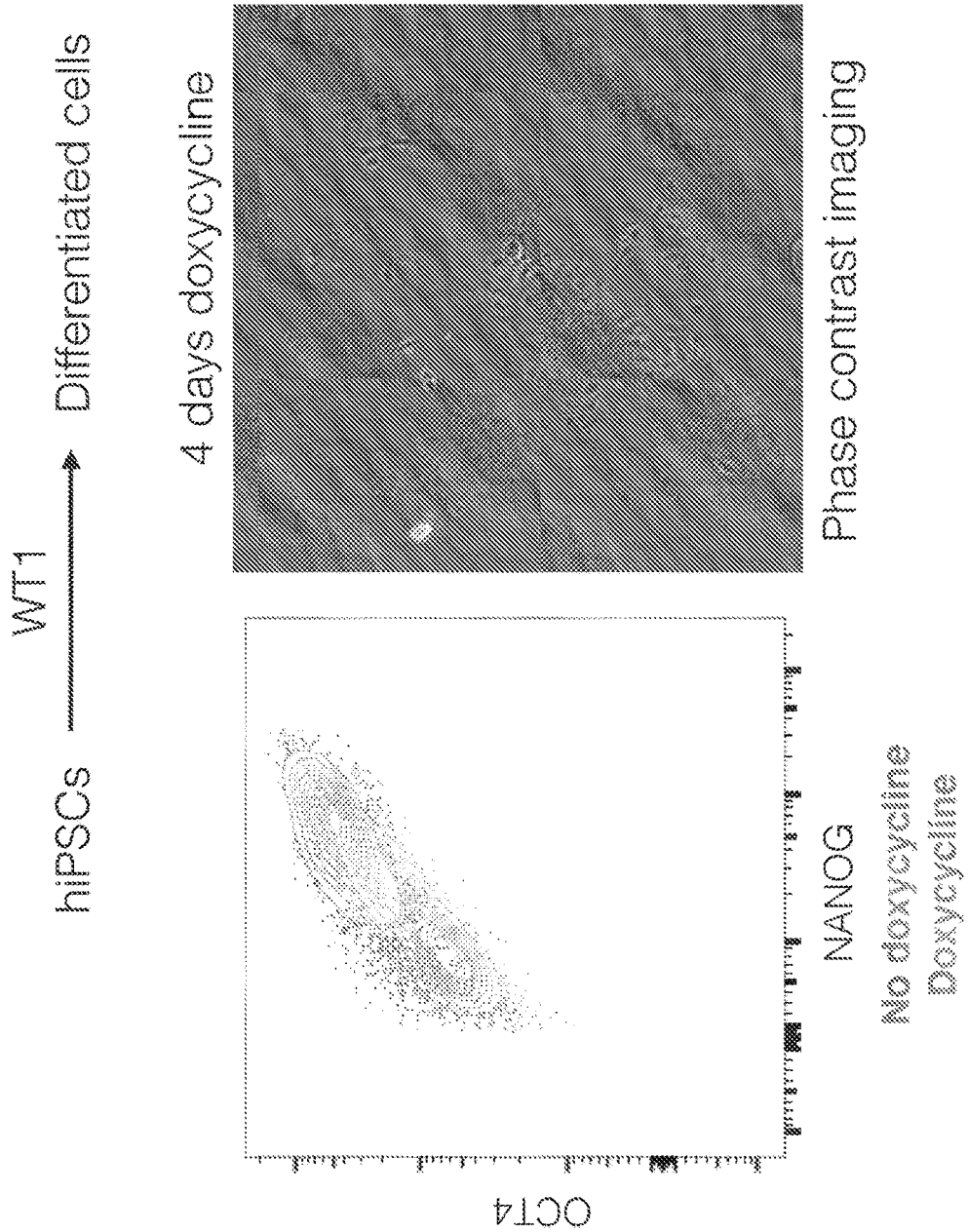
Figure 16. WT1 induces hiPSC differentiation in stem cell media without embryoid body formation, additional growth factors or mechanical manipulations

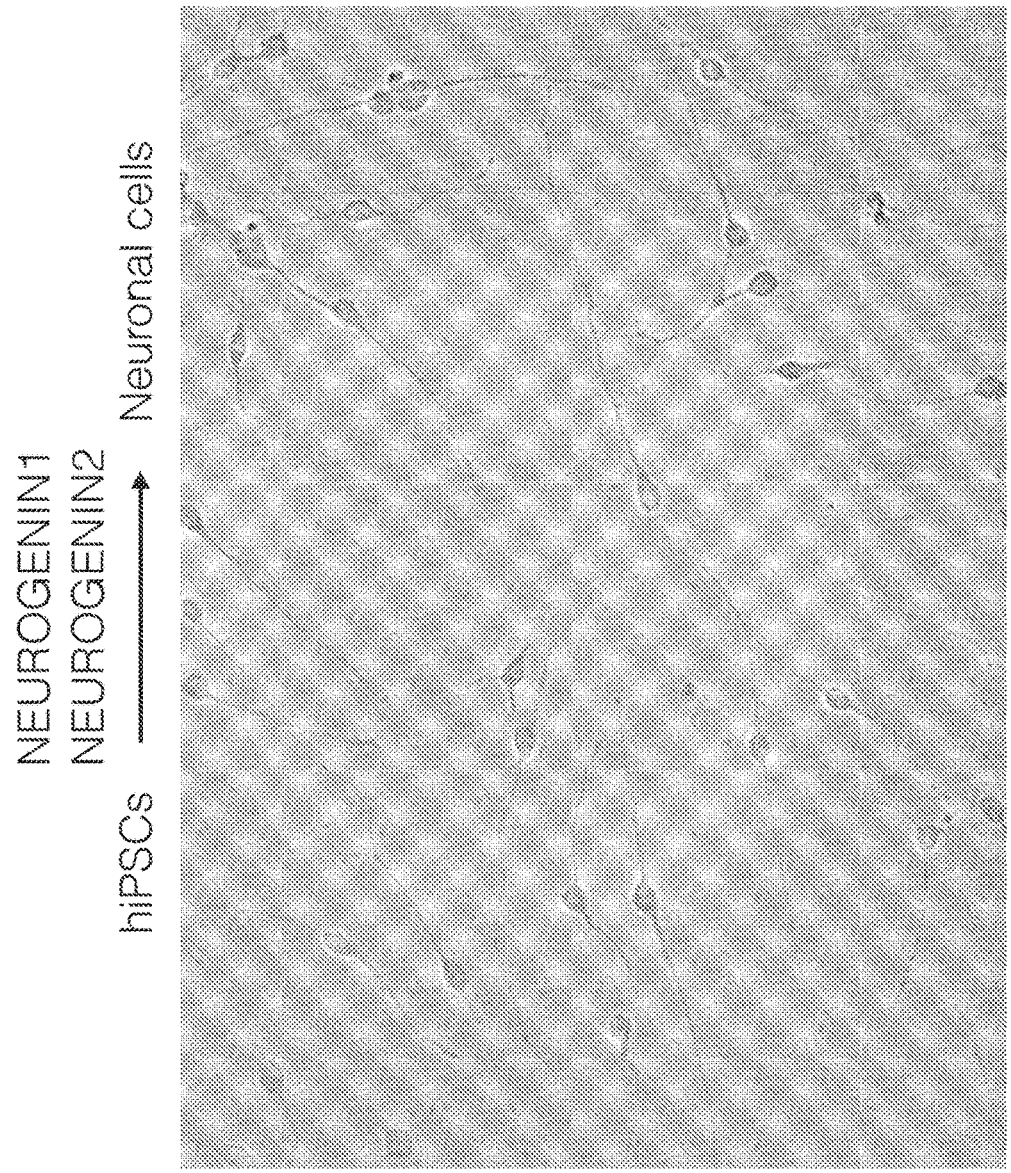
Figure 17. NEUROGENIN1 and NEUROGENIN2 induce neuronal differentiation from hiPSCs in stem cell media without embryoid body formation, additional growth factors or mechanical manipulations

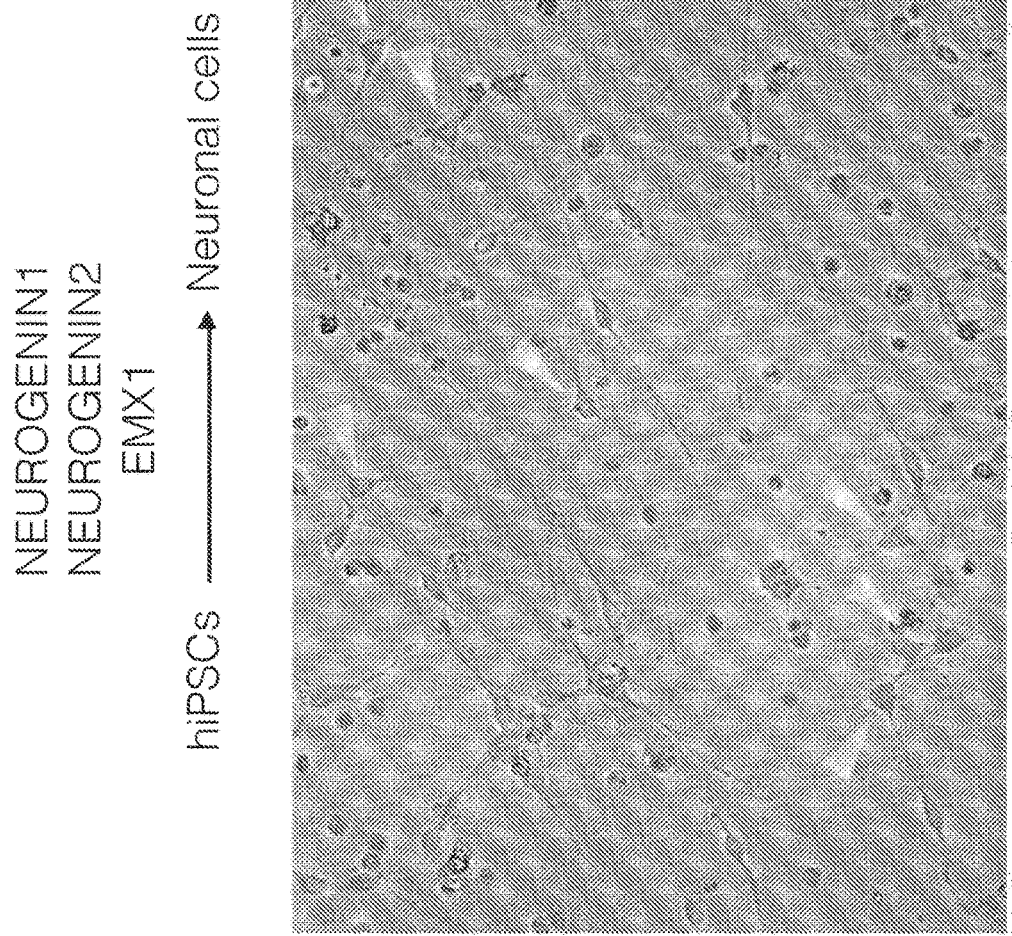
Figure 18. NEUROGENIN1 and NEUROGENIN2 and EMX1 induce cortical neuronal differentiation from hiPSCs in stem cell media without embryoid body formation, additional growth factors or mechanical manipulations

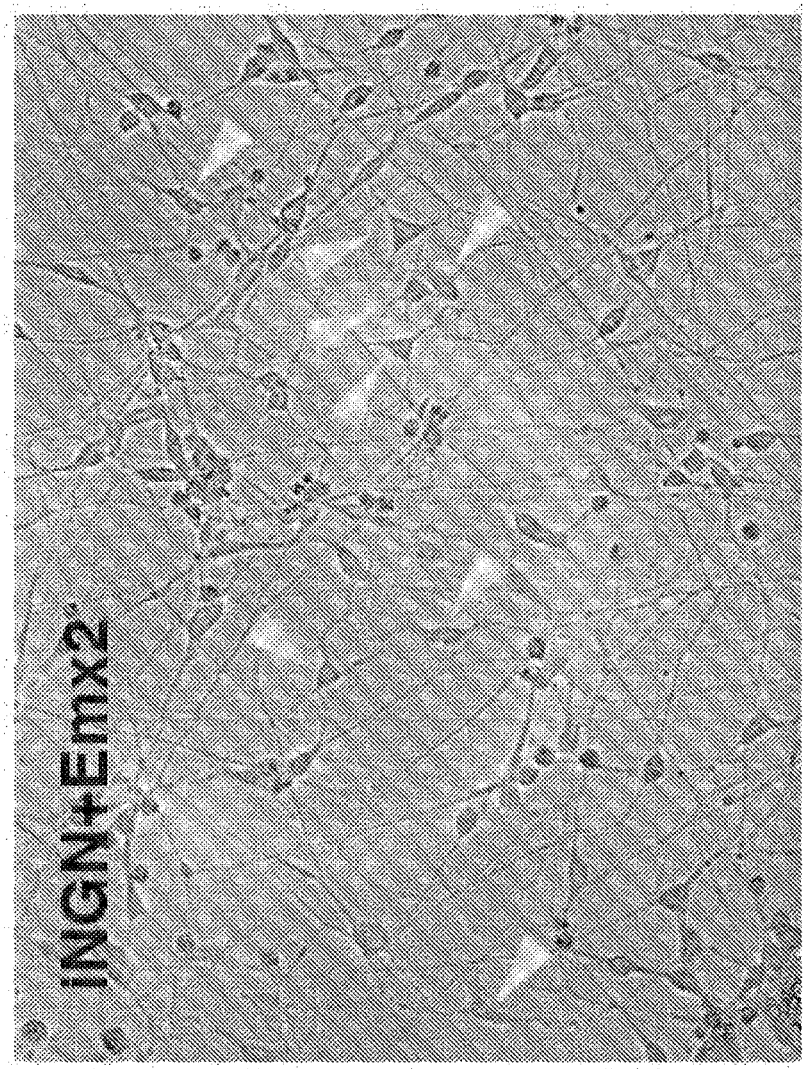
Figure 19. NEUROGENIN1 and NEUROGENIN2 and EMX2 induce cortical neuronal differentiation from hiPSCs in stem cell media without embryoid body formation, additional growth factors or mechanical manipulations

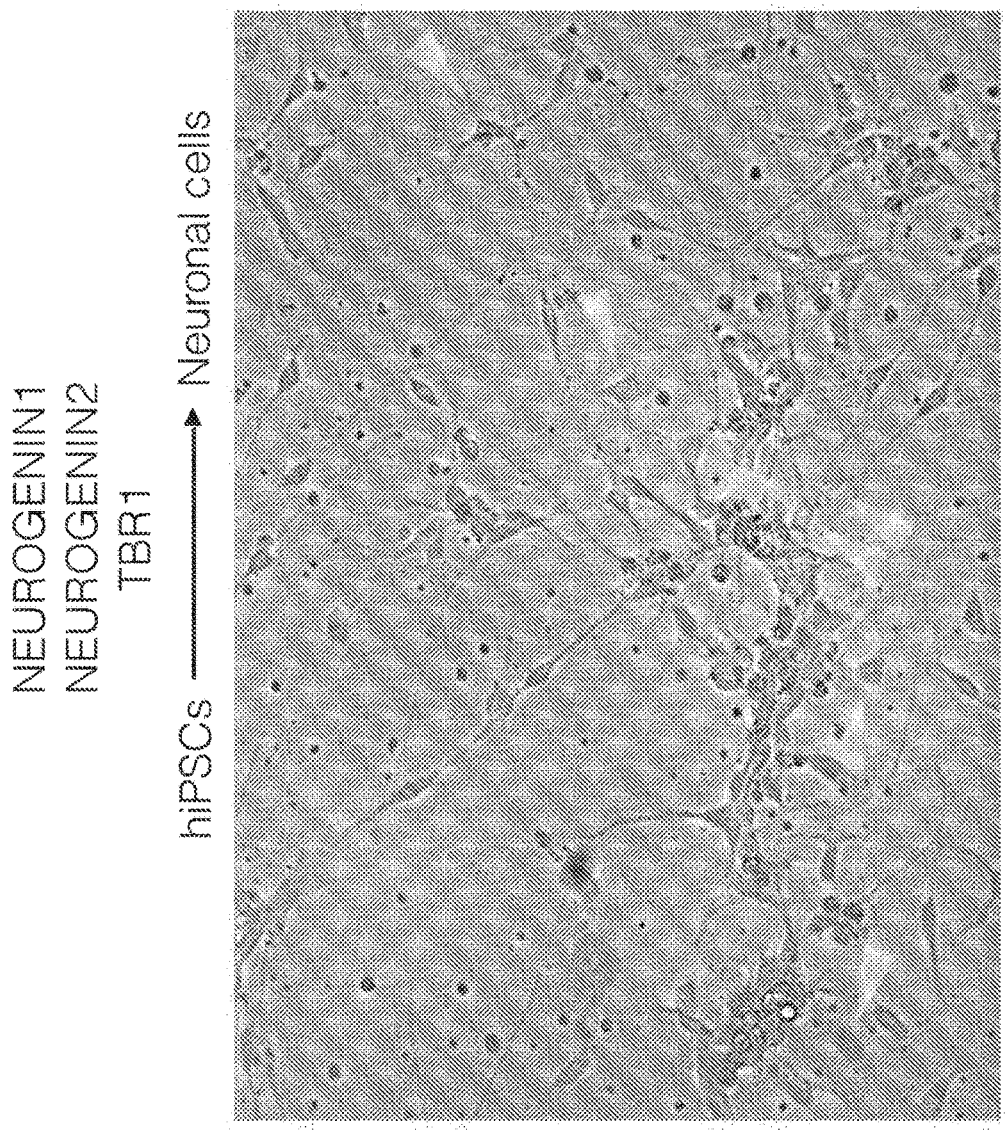
Figure 20. NEUROGENIN1 and NEUROGENIN2 and TBR1 induce cortical neuronal differentiation from hiPSCs in stem cell media without embryoid body formation, additional growth factors or mechanical manipulations

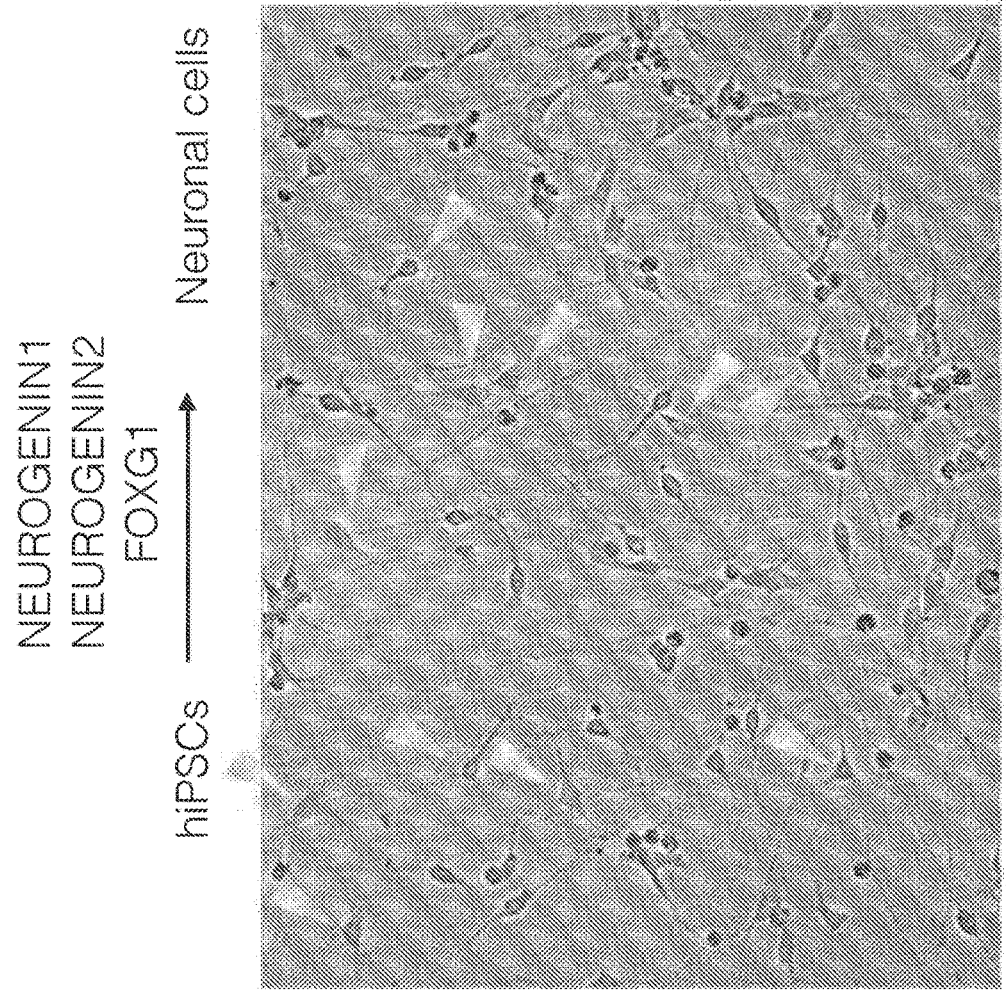
Figure 21. NEUROGENIN1 and NEUROGENIN2 and FOXG1 induce cortical neuronal differentiation from hiPSCs in stem cell media without embryoid body formation, additional growth factors or mechanical manipulations

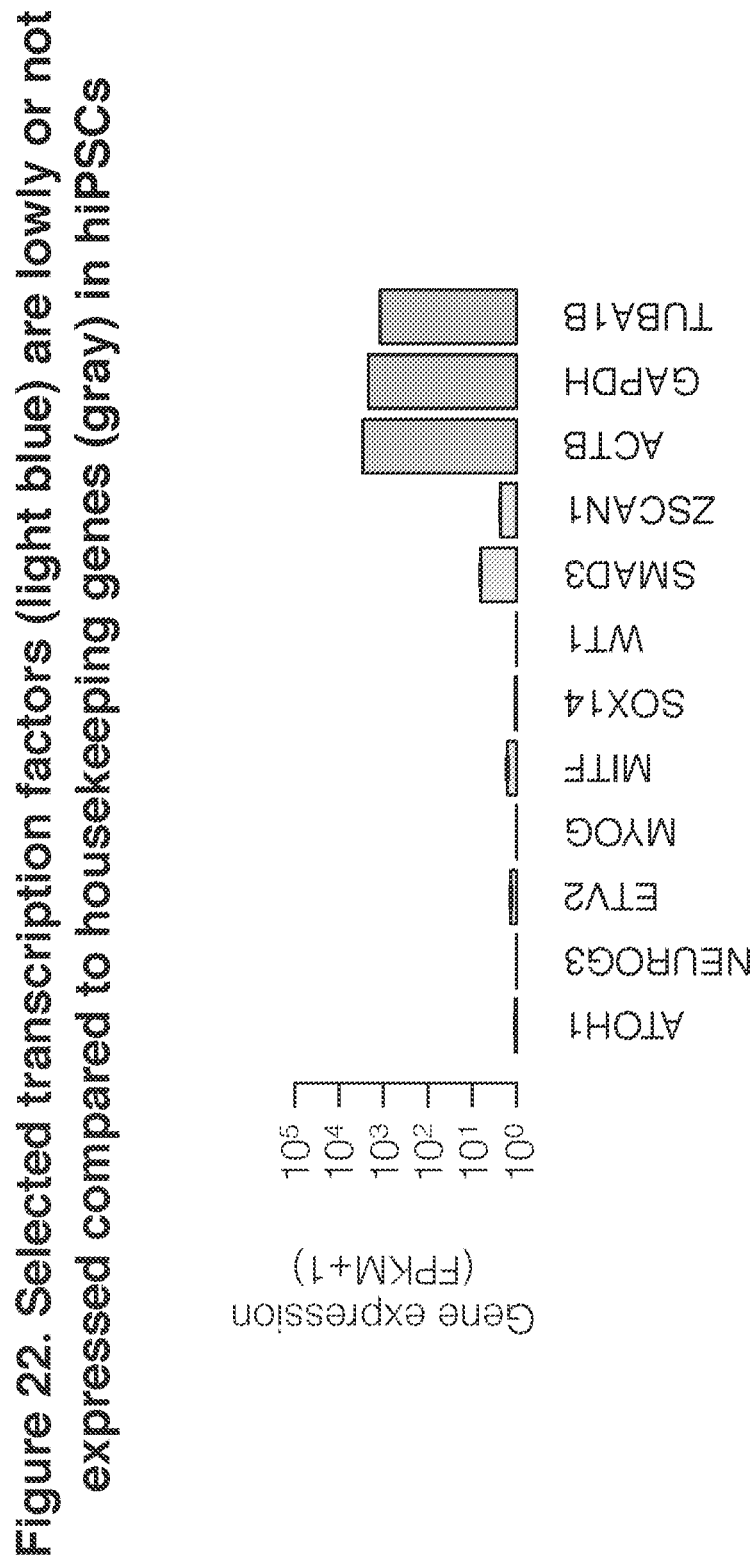
Figure 22. Selected transcription factors (light blue) are lowly or not expressed compared to housekeeping genes (gray) in hiPSCs

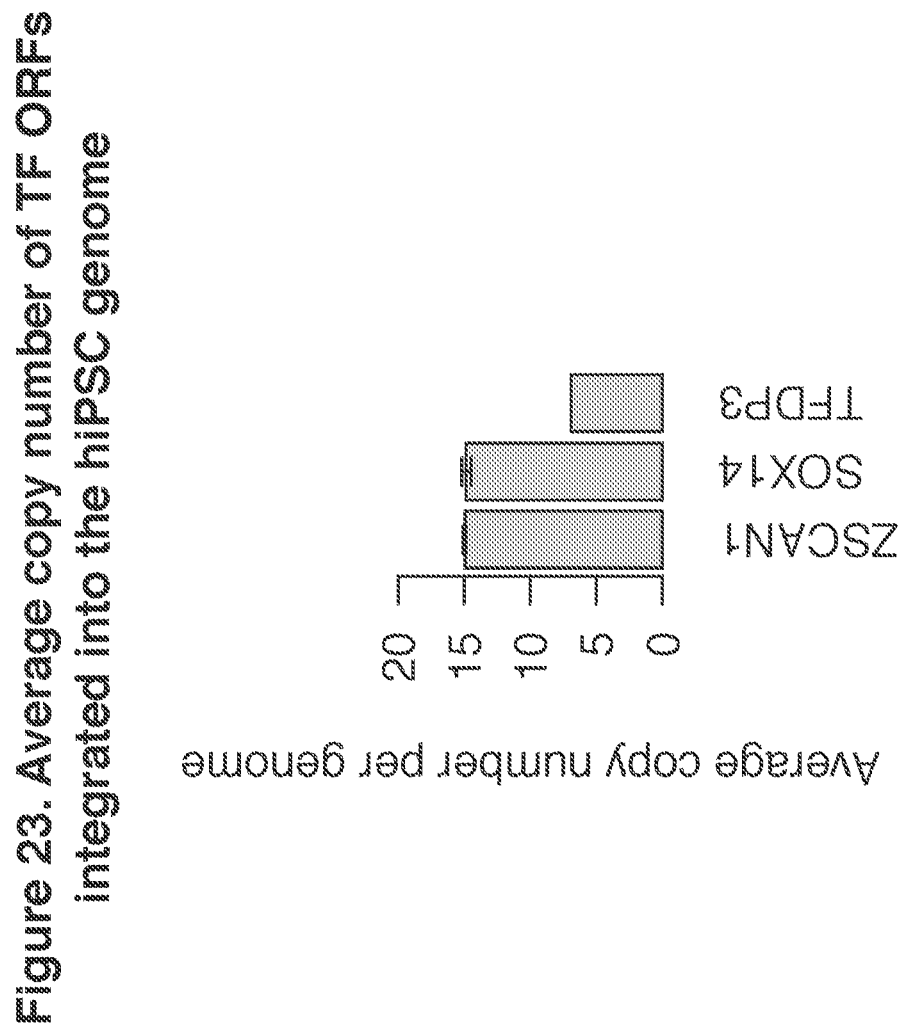
Figure 23. Average copy number of TF ORFs integrated into the hiPSC genome

TRANSCRIPTION FACTORS CONTROLLING DIFFERENTIATION OF STEM CELLS

RELATED APPLICATION DATA

This application is a national stage filing under 35 U.S.C. § 371 of International Application Serial No. PCT/US2017/051122 filed on Sep. 12, 2017, which claims the benefit under 35 U.S.C. § 119(e) of U.S. Provisional Application No. 62/393,324 filed on Sep. 12, 2016, U.S. Provisional Application No. 62/411,728 filed on Oct. 24, 2016, U.S. Provisional Application No. 62/492,552 filed on May 1, 2017 and U.S. Provisional Application No. 62/517,307 filed on Jun. 9, 2017, each of which is incorporated herein by reference in its entirety.

STATEMENT OF GOVERNMENT INTERESTS

This invention was made with government support under HG005550 and HG008525 awarded by the National Institutes of Health. The government has certain rights in the invention.

TECHNICAL FIELD OF THE INVENTION

This invention is related to the area of cell fates. In particular, it relates to induction of differentiated cells on the one hand and to the maintenance of stem cells on the other hand.

BACKGROUND OF THE INVENTION

The discovery of mouse embryonic stein cells (ESCs), human ESCs and mouse and human induced pluripotent stem cells (hiPSC) has expanded the working modes in biology: unlike studying biological phenomena such as differentiation, gaining and maintaining cellular identity in vivo, we are now theoretically able to mimic some of these processes in a dish. The use of hiPSCs facilitates studying the genesis of human cell types in an ethically approved setting, and enables production of medically relevant cell types for research and medicine. However, exploiting the full differentiation potency of stein cells is only possible with few differentiated cell types. So far, stem cell differentiation protocols are multifaceted and tailored to individual cell types. These protocols often yield highly heterogeneous populations, which may mask the cell type of interest. Whereas the initial triggers that drive stem cells out of pluripotency are known, we know very little about subsequent molecular events that occur during differentiation. For example, initial triggers include the application of differentiation media, the addition of small molecules, application of growth factors or 3D culturing techniques. These stimuli act via cellular signaling cascades and converge on transcription factors (TFs), which alter gene expression by activation and/or repression. Some of these cascades may recapitulate in vivo development, for example retinogenesis in 3D retinal organoids whereas monolayer cultures seem to follow alternative molecular differentiation routes although final cell types can have high similarity with in vivo cell types. Examples of cell identity transitions, both during the course of natural development in vivo and in synthetic in vitro systems, demonstrate the importance of controlling these transcriptional programs. The ability to control cell identity has led to the current preoccupation of the stem cell field, as facile access to primary-like human cells would enable many applications in disease modeling, drug screening and regenerative medicine. Fundamentally, the ability to find and control transitions between cell identities would greatly enhance our understanding of cell identity.

Upon obtaining a cellular identity, its maintenance is a central feature of multicellular organisms. This comprises terminally differentiated cells but also physiological stem cells, which can give rise to specific cell types in the body. To maintain the stem cell pool, transcriptional programs are active in large part by transcription factors that prevent these cells from differentiating. In vitro, maintaining the pluripotency of ESCs or iPSCs is essential to expand and maintain these cells for downstream applications. Labor-intensive and delicate culturing techniques have been developed to maintain pluripotency and to avoid spontaneous differentiation. Advances in the formulation of culture media have significantly improved the robustness of stem cell maintenance, made feeder cell co-cultures dispensable and opened the usage of stem cells to a larger scientific community.

Due to the dependence on transcriptional programs to maintain or convert cellular identities it would be desirable to gain direct control at the transcriptomic level. Detailed study of the transcriptional control of the lac operon was the first example that a certain class of DNA-binding proteins, transcription factors, initiates, enhances or represses transcription. It was shown that one could obtain transcriptional control on cell fate conversion within the same germ layer by ectopic TF expression, which was pioneered by overexpressing MyoD in fibroblasts, which subsequently converted to myoblasts, and C/EBP-alpha to convert B cells into macrophages. Forced TF induction can also convert cells arising from different germ layers, pioneered by the three TFs Brn2, Asc11 and Myt11 (BAM) that convert fibroblasts into neurons. It has also been shown that certain sets of TF can change the identity of neurons in living animals. Another striking example is the generation of iPSCs by overexpressing Oct3/4, Sox2, Klf41 and c-Myc ("Yamanaka factors") in fibroblasts. TF choices were mostly "biologically inspired;" the ones known from in vivo development were tested in vitro manually or proposed by computational approaches. This biased selection of ectopic TFs led to the successful generation of a handful of cell types. Notably, the failure rate of selected TFs to induce desired cell types from stem cells is relatively high, either not working at all or resulting in unexpected cell fates. Due to experimental and technical differences, for example gene delivery routes, transient or inducible TF expression or differences in starting cell types, we cannot easily troubleshoot these results. Since the forced TF expression in human stem cells can be very efficient, we wondered how one could confer this differentiation route systematically on producing other cell types. Obviously, one needs to standardize the technical aspects of TF delivery, expression, screening and analysis. In contrast to "biologically-inspired" TFs, an unbiased and systematic TF library screen to identify novel TFs that convert stem cells to other cell types or which reinforce pluripotency would be desirable and complementary.

So far, there have not been unbiased, systematic open reading frame (ORF) screens for converting cell identity. More recently, CRISPR-based activator screens have been performed but not for cell conversion. CRISPR-based activators for cell conversion appear to be insufficient to overcome barriers for cell identity conversion. Systematic, RNAi-based screens have revealed important pluripotency factors to understand stem cell biology, but over-expression to maintain pluripotency has not been systematically performed.

Cell types derived from human induced pluripotent stem cells (hiPSC) have high relevance for biomedical research and medicine, but robust, efficient and rapid protocols are lacking for many cell type: could we generate new protocols to generate cell types?

There is a continuing need in the art for methods of changing cell fate and maintaining cell fate so that cell populations available for cellular transplantation and drug screening can better reflect the diverse cell types in the human body.

SUMMARY OF THE INVENTION

One aspect of the invention is a method of inducing differentiation of induced pluripotent stem cells. A nucleic acid comprising an open reading frame (ORF) encoding a transcription factor, the transcription factor (TF) protein, or an activator of transcription of the gene encoding the transcription factor, is delivered to the induced pluripotent stem cells. As a consequence, the amount of the transcription factor in the induced pluripotent stem cells is increased, and the induced pluripotent stem cells differentiate to form differentiated cells.

Another aspect of the invention is a method of maintaining pluripotency of induced pluripotent stem cells. A nucleic acid comprising an open reading frame encoding the protein, the protein, or an activator of transcription of an open reading frame encoding the protein is delivered to the induced pluripotent stem cells. The protein is a transcription factor that is found in a high proportion of stem cells relative to differentiated cells after delivery of a library of transcription factors to a population of induced pluripotent stem cells. As a consequence of the delivery, the induced pluripotent stem cells maintain expression of keratin sulfate cell surface antigen, TRA-1-60, which is a marker of stem cell identity.

Another aspect of the invention is an engineered human differentiated cell that comprises one or more nucleic acids comprising an open reading frame. The one or more ORFs encodes a transcription factor selected from the group consisting of ATOH1, NEUROG3, {NEUROG1 and NEUROG2}, {NEUROG1 and NEUROG2 and EMX1}, {NEUROG1 and NEUROG2 and EMX2}, {NEUROG1 and NEUROG2 and TBR1}, {NEUROG1 and NEUROG2 and FOXG1}, ETV2, MYOG, FOXC1, SOX14, WT1, TFPD3, CDX2, SMAD3, and ZSCAN1.

Yet another aspect of the invention is an engineered human differentiated cell which comprises a nucleic acid comprising an open reading frame encoding a protein. The protein is selected from the group consisting of ZNF70; ZNF461; TFAP2B; ZNF426; MITF; CDX2; MEOX2; AKNA; NKX2-8; NKX3-2; NKX2-3; ZNF16/HZF1; ETV2; TFDP3; RELA/p65; NEUROG1; ID4; HES7; MXD4; SOX14; FOXP1; E2F2; NEUROG3; ZNF148/ZBP89; GRLF1/ARHGAP35; BOLA2; ZNF616; MAX; ATOH1; PRDM5; LHX5; ZNF273; MAFK; HOXA1; HIF2A/EPAS1; MAFB; E2F3; PRDM7; ZNF44; HMGA1; NRL; BATF3; MYOG; KLF15; LMX1A; HOXB6; DWIRTB1; ATF7; SCRT2; ZNF593; HES2; ZSCAN2; MSX2; ID3; SOX12; GLI1; DPRX; SMAD3; ZBED3; CAMTA2; MSC; ASCL3; BARX1; DMRT1; HOXA10; TSC22D3; ZNF837; MXD3; ZNF692; NHLH2; ZNF626; THAP3; SRY; WT1; SHOX; ZNF43; and ZSCAN1.

Still another aspect of the invention is an induced pluripotent stem cell which comprises a nucleic acid comprising an open reading frame encoding a protein. The protein is a transcription factor that is found in a high proportion of stem cells relative to differentiated cells after delivery of a library of transcription factors to a population of induced pluripotent stem cells. The induced pluripotent stem cell expresses keratin sulfate cell surface antigen, TRA-1-60. The transcription factor may be one or more of the group consisting of AEBP2; AIRE; ARNT2; ARNTL; ATF6; BACH1; BARX2; CASZ1; CLOCK; CREBRF; CTCFL; CXXC1; DLX2; E2F1; EBF1; EGR1; ELF4; ELF5; EMX2; ETS1; ETV1; ETV7; FEZF1; FOXJ3; FOXL2; FOXN2; FOXO1; FOXP3; FOXS1; GATA1; GCM1; HMBOX1; HOXB9; HOXC10; HOXC6; HOXD10; HOXD3; HOXD8; HSF2; HSFY1; IRF5; IRF9; IRX2; KGMF1; KLF1; KLF13; KLF16; KITS; LBX1; LCORL; MAF; MEF2A; MEIS2; MNT; MYBL2; MYF6; MYRF; NANOG; NEUROD1; NFE2L2; NFE2L3; NFIB; NFIX; NKRF; NOTO; NR0B1; NR1B1; NR1B3; NR1C2; NR1C3; NR1F3; NR1I2; NR2B2; NR2C1; NR3A1; NR3A2; NR3C4; NR5A2; OSR1; PAX6; PAX7; PAX9; PHOX2B; PKNOX1; PLAGL1; PREB; PRRX1; RBPJ; RC3H2; RFX5; SATB1; SMAD2; SMAD4; SP1; SP4; SP6; SREBF1; STAT3; TAL2; TBX14; TBX18; TBX21; TBX22; TBX5; TEAD2; TERF1; TERF2; TFAP2A; TFDP2; TFEB; THAP1; THAP10; TP63; TSHZ3; YEATS2; ZBED2; ZBTB12; ZBTB14; ZBTB17; ZBTB21; ZBTB35; ZBTB9; ZEB1; ZFHX3; ZFPM2; ZFY; ZFYVE26; ZIC4; ZKSCAN1; ZKSCAN12; ZKSCAN14; ZKSCAN19; ZKSCAN24; ZKSCAN4; ZKSCAN5; ZMAT2; ZNF114; ZNF138; ZNF146; ZNF227; ZNF253; ZNF266; ZNF280A; ZNF280C; ZNF282; ZNF296; ZNF311; ZNF317; ZNF337; ZNF34; ZNF35; ZNF350; ZNF366; ZNF396; ZNF398; ZNF41; ZNF415; ZNF460; ZNF485; ZNF497; ZNF511; ZNF512; ZNF517; ZNF543; ZNF550; ZNF586; ZNF613; ZNF615; ZNF619; ZNF641; ZNF644; ZNF645; ZNF648; ZNF655; ZNF658; ZNF662; ZNF664; ZNF669; ZNF704; ZNF740; ZNF754; ZNF75A; ZNF774; ZNF789; ZNF8; ZNF80; ZNF84; ZSCAN16; ZSCAN22; ZSCAN32; ZXDA; ZXDC; and ZZZ3.

Another aspect of the invention is a method of inducing differentiation of induced pluripotent stem cells. Increased expression is induced of a gene selected from the group consisting of ATOH1, NEUROG3, {NEUROG1 and NEUROG2}, {NEUROG1 and NEUROG2 and EMX1}, {NEUROG1 and NEUROG2 and EMX2}, {NEUROG1 and NEUROG2 and TBR1}, {NEUROG1 and NEUROG2 and FOXG1}, ETV2, MYOG, FOXC1, SOX14, WT1, TFPD3, CDX2, SMAD3, and ZSCAN1. The induced pluripotent stem cells thereby differentiate to form differentiated cells.

Yet another aspect of the invention is a method of inducing differentiation of induced pluripotent stem cells. Expression of a gene is induced. The gene is selected from the group consisting of ATOH1, NEUROG3, {NEUROG1 and NEUROG2}, {NEUROG1 and NEUROG2 and EMX1}, {NEUROG1 and NEUROG2 and EMX2}, {NEUROG1 and NEUROG2 and TBR1}, {NEUROG1 and NEUROG2 and FOXG1}, ETV2, MYOG, FOXC1, MITF, SOX14, WT1, TFPD3, CDX2, SMAD3, and ZSCAN1. The induced pluripotent stem cells thereby differentiate to form differentiated cells.

These and other embodiments which will be apparent to those of skill in the art upon reading the specification provide the art with tools and methods for controlling the cell fate of stem cell populations.

BRIEF DESCRIPTION OF THE DRAWINGS

FIG. 1. Workflow for screening the human TFome (a comprehensive expression library of 1,578 human transcription factor (TF) clones with full coverage of the major TF families) for loss of pluripotency in hiPSCs (human-induced-pluripotent-stem-cell)

FIG. 2. General strategy for high-throughput screening for cell type conversion

FIG. 3. The Human TFome expression library

FIG. 4. Expression vectors for delivery of human TFome

FIG. 5. Hits from high-throughput screening for stem cell differentiation [loss of stein cell identity (TRA-1-60) in human induced pluripotent stem cells]

FIG. 6. Hits are enriched for developmental genes and protein domains

FIG. 7. Selected transcription factors that induce stem cell differentiation

FIG. 8. ATOH1 induces neuronal differentiation from hiPSCs in stem cell media without embryoid body formation, additional growth factors or mechanical manipulations FIG. 9. NEUROG3 induces neuronal differentiation from hiPSCs in stem cell media without embryoid body formation, additional growth factors or mechanical manipulations FIG. 10. ETV2 induces endothelial differentiation from hiPSCs in stem cell media without embryoid body formation, additional growth factors or mechanical manipulations FIG. 11. MYOG induces muscle differentiation from hiPSCs in stem cell media without embryoid body formation, additional growth factors or mechanical manipulations FIG. 12. FOXC1 induces differentiation of hiPSCs in stem cell media without embryoid body formation, additional growth factors or mechanical manipulations FIG. 13. MITF induces differentiation of hiPSCs in stem cell media without embryoid body formation, additional growth factors or mechanical manipulations FIG. 14. SOX14 induces hiPSC differentiation in stem cell media without embryoid body formation, additional growth factors or mechanical manipulations FIG. 15. ZSCAN1 induces hiPSC differentiation in stem cell media without embryoid body formation, additional growth factors or mechanical manipulations FIG. 16. WT1 induces hiPSC differentiation in stem cell media without embryoid body formation, additional growth factors or mechanical manipulations FIG. 17. NEUROGENIN1 and NEUROGENIN2 induce neuronal differentiation from hiPSCs in stem cell media without embryoid body formation, additional growth factors or mechanical manipulations FIG. 18. NEUROGENIN1 and NEUROGENIN2 and EMX1 induce cortical neuronal differentiation from hiPSCs in stem cell media without embryoid body formation, additional growth factors or mechanical manipulations FIG. 19. NEUROGENIN1 and NEUROGENIN2 and EMX2 induce cortical neuronal differentiation from hiPSCs in stem cell media without embryoid body formation, additional growth factors or mechanical manipulations FIG. 20. NEUROGENIN1 and NEUROGENIN2 and TBR1 induce cortical neuronal differentiation from hiPSCs in stem cell media without embryoid body formation, additional growth factors or mechanical manipulations FIG. 21. NEUROGENIN1 and NEUROGENIN2 and FOXG1 induce cortical neuronal differentiation from hiPSCs in stem cell media without embryoid body formation, additional growth factors or mechanical manipulations FIG. 22. Selected transcription factors (first nine shown) are expressed at a low leve or not at all, compared to housekeeping genes (last three shown) in hiPSCs FIG. 23. Average copy number of TF ORFs integrated into the hiPSC genome

DETAILED DESCRIPTION OF THE INVENTION

The inventors have developed techniques for inducing differentiation of stem cells into particular cell lineages, as well as techniques for inducing stem cells to continue to proliferate as stem cells. Rather than using special growth conditions, small molecules, or growth factors, the techniques deploy transcription factors (TFs) to trigger differentiation programs or stem cell renewal programs that prevent differentiation.

As determined, certain transcription factors are able to induce stem cells to differentiate to particular lineages. For example, MITF causes stem cells to form melanocytes. Similarly, CDX2 causes stem cells to form placental cells. MYOG causes stem cells to form smooth muscle cells. An initial indicator of differentiation can be the loss of stem cell specific markers. For example, the keratin sulfate cell surface antigen, TRA-1-60, can be assayed in the cells, as it is lost early in the process of differentiation. Using loss of stem cell markers as an indicator also provides a general means for detecting relevant transcription factors, rather than looking for acquisition of a marker that is newly expressed during differentiation by a particular cell lineage. Loss-of-marker screening may be applied to cell types other than stem cells, for instance, to identify TFs that directly convert fibroblasts into cell types of interest. In some aspects, combination of transcription factors may be used to achieve differentiation to a particular cell lineage. The combination may achieve a cell type or a cell sub-type that is not achieved by either transcription factor alone. Alternatively, the combination may achieve the same cell type as one of the transcription factors alone, but may achieve it more efficiently.

Stem cells may be sorted from differentiated cells or differentiating cells by various means, typically based on differential gene expression. For example, fluorescence activated cell sorting may be used to separate cells on the basis for their expression of TRA-1-60. Alternatively, certain differentiated cells may be sorted from other differentiated cells and from cells on the basis of their expression of a lineage-specific cell surface antigen. Yet another means is by assessing expression at the RNA level, by single cell RNA sequencing without any sorting or pre-selection step. Such techniques are known in the art and may be used as is suitable and convenient for a particular application.

Any means known in the art for increasing the amount of a transcription factor in a stem cell can be used. This may involve delivery of either a nucleic acid comprising an open reading frame encoding the transcription factor, delivery of the transcription factor itself, or delivery of an activator of the transcription factor or its expression. Any technique known in the art, for such delivery may be used. For example, for delivery of a cDNA, a viral or plasmid vector may be used. The open reading frame (encoding any isoform of the TF) may be inducible or repressible for control, to achieve a suitable level of expression. The nucleic acid comprising the open reading frame may be a cDNA, an mRNA, or a synthetic or engineered nucleic acid. Some transcription factors may require a critical amount of expression to effectively induce differentiation, such as the equivalent of at least 5, 10, 15, 20, 25, or 50 copies of the ORF per cell. Other factors may require less than a certain threshold of expression due to possible toxicity at high levels, such as less than 20, 10, or 5 copies per cell. Increased levels of expression may also be achieved by increasing the copy number of air ORF, for example, by using a higher copy number vector or by using a transposon. In some embodiments, nuclease-null or "dead" Cas9 variants may be used to activate the transcription of a desired transcription factor. See, e.g., Chavez et al., *Nature Methods* 13:563-569, 2016. In other embodiments, modified RNAs—RNAs that encode the transcription factor, but use synthetic nucleotides that improve stability and reduce degradation—may be used. In some cases, use of culture media adapted for a particular cell type may increase the expression of the ORF that induces expression of that cell type. Expression of an ORF can be increased from a non-expressed gene, from a gene expressed at a low level, or from a gene expressed at a robust level. Overexpression is expression at level that is higher than the level that is expressed before induction from a gene that is expressed at a low, medium or high level.

An exogenous open reading frame is typically an open reading frame that differs from the similar gene or mRNA in the cell. It may be engineered to have a different control sequence or sequences, such as promoter, operator, enhancer, terminator, etc. It may be engineered to have no introns. It may be engineered to be fused to a second open reading frame to which it is not fused in the human genome.

The differentiated cells that can be produced using the methods described here will have multiple applications. They can be used for regenerative medicine, such as transplanting the cells into a recipient in need of a certain type of cell. They can be used for drug testing, both in cell culture as well as after transplantation. The cells may be used to deliver a product to a part of a body, for example, if they naturally produce or are engineered to produce and secrete the product.

Drug testing in the cells may use substances that are known or unknown to have a certain biological activity. The substances may be elements, compounds or mixtures, whether natural or synthetic. The cells may be used to determine a desirable activity of a potential drug or conversely to determine undesirable effects of a substance or lack of such effects. The contacting of the substance with the cells may be in culture or in a human or animal body. The activity or side effects of the substance may be determined in vitro or in vivo, irrespective of where the contacting occurred.

Changes that are observed in the cells being tested are not limited. The cells can be observed for effects on cell growth, apoptosis, secreted products, expression of particular products, etc. The genome of these cells may be edited to match mutations found in patients with disease. Any type of assay known in the art for such changes may be used, including but not limited to immunological assays, morphological observations, histochemical stains, reverse transcription polymerase chain reaction, protein blots, mass spectrometry, hybridization assays, electrophysiology, etc.

The stem cells may be obtained from source. One particularly useful source is human induced pluripotent stem cells. Mouse induced pluripotent stem cells and mouse embryonic stem cells may also be used, as well as such cells from other animals. The use of human embryonic stem cells may be regulated or ethically undesirable, but these may be used as well.

Differentiated cells may be identified by any property or set of properties that is characteristic or defining of that type of differentiated cell. For example, different cell types have a unique transcriptome. The transcriptome may be used as a means of matching and identifying an unknown cell type to a known cell type. The transcriptome may be used qualitatively or quantitatively. Similarly a proteome may be used a means of identifying an unknown differentiated cell type. Some cell types may be identifiable based on morphology, growth habit, secretion products, enzymatic activity, cellular function, and the like. Any means known in the art for identifying cells may be used.

The above disclosure generally describes the present invention. All references disclosed herein are expressly incorporated by reference. A more complete understanding can be obtained by reference to the following specific examples, which are provided herein for purposes of illustration only, and are not intended to limit the scope of the invention.

Example 1

We decided to compose a complete TF ORF library by combining factors from existing resources. Absent TFs were obtained by de nova gene synthesis. This "human TFome", comprises 1,578 canonical human TFs driven by an inducible promoter system within an all-in-one Tet-ON lentiviral vector backbone for stable integration in hiPSCs. By screening the human TFome we found over 70 TFs that induce loss of hiPSC identity, suggesting pervasive potency for TFs to alter cell identity. This resource, the entire library as well as individual TFs, will be publicly available at Addgene (non-profit plasmid repository) and a subset of hiPSC lines in which certain TB can be induced will be available. We applied the human TFome as single TFs per hiPSCs to identify individual TFs that convert stein cells to other cell identities or reinforce pluripotency. High-throughput fluorescence cell sorting (FACS) in combination with next generation sequencing and subsequent bioinformatic analyses was performed to screen for TFs in two hiPSC lines. We show that expression levels are critical and can be elevated by using transposon-mediated integration of expression cassettes. The application of the human TFome in hiPSCs resulted in the validation of over ten TFs cell fate converting TFs. Furthermore, we discovered over one hundred TFs that reinforce pluripotency, which may help to improve the robustness of stein cell cultures.

Example 2

Generating and Applying the Human TFome

Systematic and comprehensive TF-wide induction screening in human stem cells requires the availability of a TF-expression library. Notably, only partial human libraries, for example TFs included in the ORFeome, were accessible. Therefore, we decided to assemble TFs from available resources or by de novo gene synthesis to compile the "human TFome", an expression library of 1,578 TFs representing all canonical human transcription factors (Vaquerizas et al. 2009) and further curated.

The pLIX403 lentiviral vector was chosen because it allows for genomic transgene integration, doxycycline-inducible TF expression from a Tet-On system and puromycin selection of transduced cells. The individual TFs in shuttling vectors (pENTR) were cloned into pLIX403 by pooled gateway cloning. To discriminate the ectopic TFs from intrinsic expression, the TFs were marked by a V5 epitope tag translated on the backbone downstream of the Gateway recombination site on the C-terminus of the TF. The pLIX403 vector comprises a second ubiquitous promoter cassette driving the rTA3 gene needed to activate the TetOn promoter in the presence of the small molecule doxycycline and bicistronically a puromycin selection marker. About 98% of the TFs were detectable by next-generation sequencing after subcloning in the DNA plasmid library, which subsequently was used to produce lentiviral particles.

We transduced the PGP1 from the Personal Genome Project and ATCC DYS0100 human iPSC lines with the human TFome at a low multiplicity of infection (MOI=0.1), such that cells would receive a single lentiviral integration at most. In total, we transfected both cell lines each with a complete human TFome pool as well as with two subpools that we have six independent transductions. To obtain sufficient coverage of the library, we ensured that on average each TF was present in at least one hundred cells after lentiviral transduction. Genes that confer resistance to the antibiotics bleomycin, blasticidin, and hygromycin, which should not induce differentiation, were also transduced as negative controls. Transduced cells were then selected for TF-integration using puromycin, expanded and doxycycline was added for four days for continuous TF induction. FACS separated the stained population into the differentiated TRA-1-60$^{low}$ and the pluripotent TRA-1-60$^{high}$ population. For each of these populations, the integrated genes were amplified using universal primer PCR, and sequenced.

Example 3

Transcription Factors-Wide Screening for Alterations in Pluripotency in Human Induced Pluripotent Stem Cells To identify TFs that induce stem cells into any differentiated cell, we devised a strategy to screen for individual TFs that potently cause loss of pluripotency rather than enriching for cells with any specific cell type marker. We used a fluorescence-activated cell sorting (FACS) approach, which enables multiplexed assessment of the human TFome followed by TF identification by using next-generation sequencing. To measure the loss of pluripotency, we stained for the keratin sulfate cell surface antigen TRA-1-60, which is rapidly lost upon exit from pluripotency. Importantly, because we aimed to identify potent inducers of differentiation, we performed the screen in the standard mTeSR1 stem cell media.

We first aimed to comprehensively identify single TFs that would induce loss of pluripotency. To score each TF for its differentiation potential, we computed a ratio of each TF by dividing the number of normalized reads sequenced in the differentiated TRA-1-60$^{low}$ population versus the pluripotent TRA-1-60$^{high}$ population. We expect a TF that induces differentiation to be highly enriched in the TRA-1-60$^{low}$ population compared to the pluripotent TRA-1-60$^{high}$ population, and hence have a high ratio. Conversely a TF that reduces spontaneous differentiation, for instance by maintaining pluripotency, would have fewer reads in the differentiated population compared to the pluripotent population. We set a threshold for a TF having no effect based on the score of the truncated fluorescent proteins. TFs that increase cell proliferation without affecting pluripotency would be expected to have differentiation scores similar to these truncated fluorescent proteins.

Based on this differentiation scoring metric, we identified over 70 TFs that induce loss of pluripotency ("differentiation-inducing TFs") and over 100 TFs that reinforce pluripotency ("pluripotency-reinforcing TFs"), as compared to the truncated fluorescent protein controls. To assess the quality of this screen, we conducted gene set enrichment analysis (GSEA) on the differentiation-inducing TFs. We discovered that differentiation-inducing TFs are enriched for developmental processes and system development, which is consistent with their ability to induce loss of pluripotency in our screen. In terms of protein domains, basic helix-loop-helix DNA-binding domains, which are often present in TFs involved in development were enriched, whereas, zinc fingers and Küppel-associated box (KRAB) domains were depleted. Overall, these results suggest that our screen in human stem cells recovers developmentally important TFs that have been identified in model organisms in vivo.

Example 4

Transcription Factors Induce Rapid and Efficient Differentiation when Expressed at High Levels To craft genetic recipes that rapidly and efficiently induce hiPSCs into cell types, we engineered inducible single-TF expressing cell lines that could produce cell types of interest on demand. We originally aimed to mimic closely the conditions of the screen, namely single-copy lentiviral integration. Our initial efforts successfully validated the screen, however the differentiation efficiencies were weak (~10%), similar to CRISPR-Cas9 activator-based differentiation experiments. To overcome this challenge while keeping with our goal for simple differentiation protocols without additional growth factors, mechanical steps or selections, we wondered whether low TF expression levels of the integrated lentiviral vector was the bottleneck of highly efficient differentiation. We surmised that certain crucial target genes may be occluded with a low probability of TF binding and activation of transcription; thus a higher expression would in theory increase the probability of a successful binding and hence transcriptional event that may activate positive feedback loops that induce exit from pluripotency.

To express high levels of TF, we first tested transduction with high titer lentiviral particles, which resulted in massive cell death. To improve the transduction efficiency and the vialibility of hiPSCs, we constructed a PiggyBac transposon-based vector with similar doxycycline-inducible TF expression and the ability to use puromycin to select for transduced cells. Critically, this transposon system allows for facile high-copy integration of TFs; in our hands, we average ~15 integrated copies per genome, as assessed by digital droplet PCR. Due to this integration efficiency, it is challenging to set copy numbers to a single TF per cell. Therefore, we decided not to repeat the screen with the lentiviral system but selected Trs that had a high differentiation score for subcloning into the PiggyBac vectors.

Using this high expression system, we assessed differentiation efficiency. By bright-field microscopy, we observed a rapid loss of stem cell morphology, specifically migration away from colonies and adoption of distinct cell morphologies. We quantified loss of stem cell identity by intracellular flow cytometry for NANOG, OCT4 and SOX2. Uninduced stem cells had >90% NANOG$^+$ OCT4$^+$ SOX2$^+$ cells, whereas doxycycline-induced cells had <10% NANOG$^+$ OCT4$^+$ SOX2$^+$ cells.

Example 5

Systematic Classification of TF-Induced Lineages

Next, we needed an approach of identifying a priori the cell lineage being generated we needed a method analogous to BLAST, but for tissue profiles. Several studies have been published that generally compare gene expression profiles to infer common drug targets, disease mutation effects, etc; however, the broad range of genes did not allow for rigorous and unambiguous identification of cell lineage against expression profiles catalogued in the Gene Expression Omnibus. A BLAST-like approach also requires an extensive reference panel to compare to; however the mechanistic gene regulatory network-based algorithm CellNet requires many samples per tissue, which is not currently available. We systematically use thousands of RNA-seq datasets from many tissues as training data. We adapted KeyGenes, a machine-learning-based algorithm, to systematically BLAST our transcriptomes against high-quality tissue expression datasets.

The TFs that induce loss of stem cell identity may be caused by conversion into differentiated cell types, or general loss of cell identity without a specific identity. To systematically determine what lineage these TF may be inducing, we first needed a systematic approach to classify cell types. We curated a set of large-scale human tissue expression profile studies to train a machine learning classifier for cell types. This curation comprises RNA-seq samples representing tissues from the GTEx study, Human Protein Expression Atlas and Illumina Human Body Map. We then applied this as training data for KeyGenes, LASSO regression-based classifier for cell type identification.

To determine what cell lineages are being generated by these TFs, we performed RNA-seq on each cell population and used them as query for the expanded KeyGenes classifier.

Interestingly, expression of these TFs in adult human tissue did not predict which lineages were produced in hiPSCs. For instance, ETV2 induces endothelial differentiation but is most highly expressed in the testis, ATOH1 activated a neuronal cell identity but is highly expressed in the colon and small intestine, and CDX2 induced a placental identity, but is also highly expressed in the colon and small intestine. Thus observational studies alone do not appear to predict which TFs can induce which lineages, and suggest that synthetic methods of converting cell type do not necessarily recapitulate in vivo development.

Expression of specific markers for these cell lineages was present from the RNA-seq data). To enhance differentiation into these lineages, we induced TF expression in the presence of standard culturing conditions for those lineages, and assess conversion efficiency for lineage-specific markers by flow cytometry. Morphologies and lineage-specific marker expression were tested by immunohistochemical stainings. Together, these data indicate that TF-derived cells can be potently and rapidly generated.

Example 6

Experimental Methods

Annotation and Manual Curation of the TFome

Canonical human transcription factors were previously annotated by Vaquerizas et al. 2009) based on a computation search for genes that bind DNA in a sequence-specific manner, but are not enzymatic and do not form part of the core initiation complex, resulting in 1,591 TFs (classified as "a" and "b", which have experimental evidence for regulatory function, and "other" as probable TIA with undefined DNA-binding domains; class "x" was excluded as having promiscuous DNA-binding domains). We further included TFs that were predicted but did not have experimental evidence (class "c"). The following major TF families were filled in according to HUGO Gene Nomenclature Committee (HGNC): zinc finger (includes C2H2-containing domains), homeodomain (includes LIM, POU, TALE, HOXL, NKL, PRD sub-families), basic helix-loop-helix and forkhead. Pseudogenes as annotated by HGNC were removed. Duplicated and unmapped genes were removed, and all genes were converted to approved gene names using the HG-NC multi-symbol checker. The final target set of TFs in the human TFome contains 1,578 genes.

Assembly and Quality Control of the Human TFome

All TFs are cloned in pDONR-series standardized Gateway-compatible vector, building on Yang et al. 2011, Jolma et al., transOMIC technologies cDNAs, ORB (transOMIC Inc), DNA Repository at Arizona State University, and codon-optimized synthesis by Gen 9.

Pooled Cloning of the Human TEome into pLEX403 Viral Vector

To perform pooled LR cloning into the pLfX403 viral expression vector (Addgene 41395), each 96-well plate of DNA was combined into its own sub-pool and quantified using Qubit dsDNA Broad Range Assay Kit (Invitrogen Q32853). 75 ng of pENTR-TFome subpool was used for a LR Clonase II (Invitrogen 11791100) reaction overnight and digested with Proteinase K. 1 µL of the reaction was transformed into One Shot Stb13 chemically competent cells (Invitrogen C737303), plated onto a 50 cm$^2$ LB Agar plate with 100 µg/mL Carbenicillin and incubated overnight at 30° C. Serial dilutions were performed to estimate the number colonies per plate. Approximately 10,000 to 20,000 colonies grew per plate, representing 100 to 200-fold coverage per 96-member sub-pool.

Colonies from each sub-pool plate were scraped and DNA was extracted using QIAGEN Plasmid Plus Midi Kit (QIAGEN 12943) to generate pLIX403-TFome subpools. To cloning efficiency and library coverage, pENTR and pLIX403 subpools were pooled to generate pENTR-TFome and pLIX403-TFome. 5 µg of each pool was sheared to 200 bp on a Covaris S2, and 1 µg was used for library preparation using NEBNext Ultra DNA Library Prep Kit for Illumina (NEB E7370L).

Lentiviral Production and Transduction

Lentiviruses were produced as before using 45 µg DNA for two 15 cm dishes. hiPSCs were transduced with TFome lentiviruses at a multiplicity of infection (MOI)=0.1.

Flow Cytometry Analysis and Fluorescence Activated Cell Sorting (FACS)

Cells were trypsinized, washed and resuspended in FACS buffer (PBS with 10% FBS). For surface antigens, live cells were stained with fluorophore-conjugated antibodies and viability dye CellTrace Calcein Blue, AM (Life Technologies, C34853) at $1 \times 10^7$ cells/mL for 30 minutes on ice in the dark. For intracellular staining, cells were fixed using BD Cytofix fixation buffer (BD Biosciences, 554655) at $1 \times 10^7$ cells/mL for 20 minutes, washed with BD Perm/Wash buffer (BD Biosciences, 554723), and permeabilized in BD Perm/Wash buffer for 10 minutes, then stained with antibodies and DAPI in the dark for 30 minutes. Stained cells were washed twice with FACS buffer, filtered into a strainer-capped tube (Falcon, 352235) and run on a BD LSRFortessa. Compensation for spectral overlap was determined by staining AbC Total Antibody Compensation Beads (Life Technologies, A10497) with single fluorophore-conjugated antibodies.

Transcriptome Library Preparation and Sequencing

TRizol (Life Technologies, 15596-018) was added directly to cells and incubated for 3 minutes and used for RNA extraction using Direct-zol RNA MiniPrep (Zymo Research, R2050). RNA was quantified by Qubit RNA HS Kit (Molecular Probes, Q32852). 1 µg was used for Poly(A) isolation using Poly(T) beads (Bioo Scientific, 512979) and used for RNA-seq library preparation with unique molecular identifiers (UMIs) using NEXTflex Rapid Directional qRNA-seq kit (Bioo Scientific, 5130-02D). Libraries Were amplified on a LightCycler real-time quantitative PCR machine (Roche) by spiking in SYBR Gold (Life Technologies, S11494). Mid-logarithm amplified libraries were collected and purified using AMPure XP beads (AgencourtN63881), Libraries were quality controlled by TapeStation (Agilent) and quantitative PCR (KAPA Biosystems).

Transduction and Generation of Stable Cell Lines

For individual PiggyBac transductions, cells 500,000 to 800,000 cells were nucleofected using Nucleofector P3 solution (Lonza, V4XP-3032) using the Nucleofector Puromycin-resistant cells were selected and expanded.

We claim:

1. A method of screening one or more transcription factors to identify one or more transcription factors ("TF") that induce differentiation of induced pluripotent stem cells, comprising:
   delivering to the induced pluripotent stem cells
   (1) a transcription factor,
   (2) a nucleic acid molecule comprising an open reading frame encoding the transcription factor, or
   (3) an activator of transcription of a nucleic acid molecule comprising an open reading frame encoding the transcription factor, or any combination of (1)-(3), and
   identifying a transcription factor for differentiating one or more of the induced pluripotent stem cells to generate one or more differentiated cells when a ratio between a frequency of normalized reads of the transcription factor in a differentiated cell and a frequency of normalized reads of the transcription factor in an undifferentiated cell yields a Log2 score of greater than or equal to −2.02.

2. The method of claim 1, wherein the transcription factor for differentiating one or more of the induced pluripotent stem cells comprises ETV2 and endothelial cells are formed; the transcription factor for differentiating one or more of the induced pluripotent stem cells comprises MYOG and muscle cells are formed; the transcription factor for differentiating one or more of the induced pluripotent stem cells comprises FOXC1 and cardiac muscle progenitor cells are formed; the transcription factor for differentiating one or more of the induced pluripotent stem cells comprises MITF and neural crest and melanocyte cells are formed; the transcription factor for differentiating one or more of the induced pluripotent stem cells comprises WT1 and kidney progenitor cells are formed; or the transcription factor for differentiating one or more of the induced pluripotent stem cells comprises CDX2 and placental cells are formed.

3. The method of claim 1, further comprising: contacting the differentiated cells with a test substance and observing a change in the differentiated cells induced by the test substance.

4. The method of claim 1, further comprising: transplanting the differentiated cells into a patient.

5. The method of claim 4, wherein the induced pluripotent stem cells are derived from somatic cells of the patient.

6. The method of claim 4, further comprising: contacting the differentiated cells with a test substance and observing a change in the differentiated cells induced by the test substance.

7. The method of claim 6, wherein the contacting is performed before the transplanting or after the transplanting.

8. The method of claim 1, wherein the transcription factor for differentiating one or more of the induced pluripotent stem cells is selected from the group consisting of ZNF70; ZNF461; TFAP2B; ZNF426; MITF; CDX2; MEOX2; AKNA; NKX2-8; NKX3-2; NKX2-3; ZNF16/HZF1; ETV2; TFDP3; RELA/p65; NEUROG1; ID4; HEST; MXD4; SOX14; FOXP1; E2F2; NEUROG3; ZNF148/ZBP89; GRLF1/ARHGAP35; BOLA2; ZNF616; MAX; ATOH1; PRDMS; LHXS; ZNF273; MAFK; HOXA1; HIF2A/EPAS1; MAFB; E2F3; PRDM7; ZNF44; HMGA1; NRL; BATF3; MYOG; KLF15; LMX1A; HOXB6; DMRTB1; ATF7; SCRT2; ZNF593; HES2; ZSCAN2; MSX2; ID3; SOX12; GLI1; DPRX; SMAD3; ZBED3; CAMTA2; MSC; ASCL3; BARX1; DMRT1; HOXA10; TSC22D3; ZNF837; MXD3; ZNF692; NHLH2; ZNF626; THAP3; SRY; WT1; SHOX; ZNF43; NEUROG2; EMX1; EMX2; TBR1; FOXG1; FOXC1; TFPD3; and ZSCAN1.

9. The method of claim 8, further comprising sorting the differentiated cells using fluorescence activated cell sorting.

10. The method of claim 9, further comprising:
    assaying the differentiated cells and determining a set of transcribed genes;
    comparing the set of transcribed genes of the differentiated cells to one or more reference sets of transcribed genes from one or more reference tissues or cells; and
    identifying a match between the differentiated cells and a reference tissue or cell.

11. The method of claim 9, further comprising:
    assaying the differentiated cells and determining amounts of a set of transcribed genes;
    comparing the amounts of the transcribed genes of the differentiated cells to one or more reference sets of amounts of transcribed genes from one or more reference tissues or cells; and
    identifying a match between the differentiated cells and a reference tissue or cell.

12. The method of claim 9, further comprising:
    identifying differentiated cells as a type of differentiated cells by assaying morphological features of the differentiated cells and matching the morphological features to morphological features of a reference tissue or cell;
    identifying differentiated cells as a type of differentiated cells by assaying protein marker expression of the differentiated cells and matching the protein marker expression to a reference tissue or cell's protein marker expression; or
    identifying differentiated cells as a type of differentiated cells by assaying a function and matching the function to a function of a reference tissue or cell.

13. The method of claim 9, wherein the differentiated cells are sorted on the basis of loss of expression of a stem cell marker.

14. The method of claim 13, wherein the stem cell marker is keratin sulfate cell surface antigen, TRA-1-60.

15. The method of claim 13, wherein the loss of expression of a stem cell marker is determined in a medium adapted for growth of stem cells.

16. The method of claim 1, wherein the nucleic acid molecule is a cDNA and expression of the cDNA is inducible.

17. The method of claim 1, wherein the nucleic acid molecule is a cDNA and multiple copies of the cDNA per genome are integrated in the genome of the induced pluripotent stem cells.

18. The method of claim 1, wherein the transcription factor, the nucleic acid molecule comprising the open reading frame encoding the transcription factor, or the activator of transcription of the nucleic acid molecule comprising the open reading frame encoding the transcription factor are present in the differentiated population of cells.

\* \* \* \* \*